(12) United States Patent
Isanaka

(10) Patent No.: US 10,538,561 B2
(45) Date of Patent: Jan. 21, 2020

(54) PEPTIDE FOR TREATING INFLAMMATORY DISEASES

(71) Applicant: Isanaka Ram, Hyderabad (IN)

(72) Inventor: Ram Isanaka, Hyderabad (IN)

( * ) Notice: Subject to any disclaimer, the term of this patent is extended or adjusted under 35 U.S.C. 154(b) by 0 days.

(21) Appl. No.: 15/545,427

(22) PCT Filed: Jan. 21, 2016

(86) PCT No.: PCT/IN2016/000025
§ 371 (c)(1),
(2) Date: Jul. 21, 2017

(87) PCT Pub. No.: WO2016/116948
PCT Pub. Date: Jul. 28, 2016

(65) Prior Publication Data
US 2018/0009860 A1 Jan. 11, 2018

(30) Foreign Application Priority Data
Jan. 22, 2015 (IN) .............................. 312/CHE/2015

(51) Int. Cl.
*A61K 38/20* (2006.01)
*C07K 14/54* (2006.01)
*C07K 14/47* (2006.01)
*A61K 38/00* (2006.01)

(52) U.S. Cl.
CPC .......... *C07K 14/4703* (2013.01); *A61K 38/20* (2013.01); *C07K 14/54* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,091,310 B2 | 8/2006 | Merzouk et al. | |
| 2006/0233748 A1* | 10/2006 | Merzouk ............ | A61K 38/2053 424/85.2 |
| 2010/0144641 A1* | 6/2010 | Popel ...................... | C07K 14/47 514/6.9 |
| 2012/0270770 A1 | 10/2012 | Jaynes | |
| 2013/0210707 A1 | 8/2013 | Chung et al. | |
| 2013/0296250 A1 | 11/2013 | Braiman-Wiksman et al. | |
| 2013/0310309 A1 | 11/2013 | Primor | |
| 2014/0170138 A1 | 6/2014 | Naparstek et al. | |
| 2014/0220030 A1 | 8/2014 | Sveinsson | |

FOREIGN PATENT DOCUMENTS

| EP | 16545427 A2 | 4/2006 | |
|---|---|---|---|
| WO | WO-2007033215 A2 * | 3/2007 | ............. C07K 14/47 |
| WO | 2014201034 A2 | 12/2014 | |

OTHER PUBLICATIONS

Moutinho et al., "Nanocarrier possibilities for functional targeting of bioactive peptides and proteins: state-of-the-art," J. Drug Targeting 20:114-141 (2012).*
WHO Cardiovascular guidelines "Prevention of Cardiovascular Disease: Guidelines for assessment and management of cardiovascular risk" accessed at Mar. 16, 2015 at URL who.intJcardiovascular_diseases/guidelines/Full%20text.pdf.*
Medline Plus, obesity, available at http://www.nlm.nih.gov/medlineplus/obesity.html—(referenced Aug. 22, 2013).*
St. John Providence Health Center; Preventing Obesity; http://www.stjohnprovidence.org/HealthInfoLib/swarticle.aspx?type=85&id=P07863 (referenced Aug. 22, 2013).*
EMedicine Health, diabetes causes, http://www.onhealth.com/diabetes_health/page3.htm#diabetes_causes (referenced Aug. 22, 2013).*
United Healthcare, diabetes, http://www.uhc.com/source4women/health_topics/diabetes/relatedinformation/d0f0417b073bf110VgnVCM1000002f10b10a___.htm—referenced Aug. 22, 2013.*
Weiner, "Multiple sclerosis is an inflammatory T-cell-mediated autoimmune disease," Arch. Neurol. 61:1613-1615 (2004).*
Arican et al., Serum Levels of TNF-α, IFN-γ, IL-6, IL-8, IL-12, IL-17, and IL-18 in Patients With Active Psoriasis and Correlation With Disease Severity, Mediators Inflamm. 5:273-279 (2005).*
Harada et al., "Interleukin 8 as a novel target for intervention therapy in acute inflammatory diseases," Mol. Med. Today 2:482-489 (1996).*
Nanki et al., "Chemokines Regulate IL-6 and IL-8 Production by Fibroblast-Like Synoviocytes from Patients with Rheumatoid Arthritis," J. Immunol. 167:5381-5385 (2011).*
Jaynes et al., "Structure/Function Link Between Cytokine Domains and Natural and Designed Lytic Peptides: Medical Promise," Chpt 2, pp. 21-45, Small Wonders: Peptides for Disease Control, ACS Symposium Series, vol. 1095, (2012).*
Fitch, Erin, BA, et al., "Pathophysiology of Psoriasis: Recent Advances on IL-23 and Th17 Cytokines," Curr Rheumatol Rep.; Dec. 2007, pp. 1-12, 9(6): 461-467.
Griffiths, Christopher E. M., et al., "Pathogenesis and ciinical features of psoriasis," The Lancet; Jul. 21, 2007, pp. 263-271, vol. 370, No. 9538.
International Preliminary Report on Patentability; International Application No. PCT/IN2016/000025, International Filing Date: Jan. 21, 2016; Date of Completion: Jan. 26, 2017; 12 pages.
International Search Report; International Application No. PCT/IN2016/000025; International Filing Date: Jan. 21, 2016; dated May 31, 2016; 5 pages.
Liu, et al., "Review: Psoriasis: genetic associations and immune system changes," Genes and Immunity; 2007, pp. 1-12; vol. 8.
Mrowietz, U., et al, "Definition of treatment goals for moderate to severe psoriasis: a European consensus," Arch Dermatol Res; 2011, pp. 1-10, vol. 303.
Nograles, Kristine E., et al., "Anti-cytokine therapies for psoriasis," Experimental Cell Research 317, 2011, pp. 1293-1300.
Rapp, PhD, Stephen R., et al., "Psoriasis causes as much disability as other major medical diseases," J. American Acdmy. of Dermatology; Sep. 1999, pp. 401-407, vol. 41, No. 3, Part 1.
Raychaudhuri, Siba Prasad, et al., "Neuropeptides and Neurogenic Inflammation in Psoriasis," Psoriasis—Third Edition, Revised and Expanded; 1998, pp. 383-391.

(Continued)

*Primary Examiner* — Julie Ha
*Assistant Examiner* — Kristina M Hellman
(74) *Attorney, Agent, or Firm* — Cantor Colburn LLP

(57) ABSTRACT

The present invention provides a peptide having anti-inflammatory activity. The present invention also provides the method of preparation of the peptide and compositions, and kits comprising the peptide. The invention further provides the method of treating inflammatory diseases employing the peptide of the present invention.

3 Claims, 27 Drawing Sheets
Specification includes a Sequence Listing.

(56) References Cited

OTHER PUBLICATIONS

Schon, M.D., Michael P., et al, "Psoriasis," The New England Journal of Medicine, 2005, pp. 1899-1912, vol. 352;18.

Written Opinion; International Application No. PCT/IN2016/000025; International Filing Date: Jan. 21, 2016; dated May 31, 2016. 5 pages.

Zheng, Yan, et al., "Interleukin-22, a Th17 cytokine, mediates IL-23-induced dermal inflammation and acanthosis," Nature; Feb. 8, 2007, pp. 648-651; vol. 445, No. 7128.

Arican, Ozer et al.; "Serum Levels of TNF-α, IFN-γ, IL-6, IL-8, IL-12, IL-17, and IL-18 in Patients With Active Psoriasis and Correlation with Disease Severity"; Mediators of Inflammation, 5, 2005, p. 273-279.

Blake, S.J. et al.; "Role of IL-17 and IL-22 in autoimmunity and cancer" ACTAS Dermosifiliogr., 2014, 105:Supl 1, p. 41-50.

Boutet, Marie-Astrid et al.; "Role of the IL-23/IL-17 Axis in Psoriasis and Psoriatic Arthritis: The Clinical Importance of Its Divergence in Skin and Joints"; International Journal of Molecular Sciences, 19, 2018, p. 1-27.

Bromley, Shannon K. et al.; "IL-23 Induces Atopic Dermatitis-Like Inflammation Instead of Psoriasis-Like Inflammation in CCR2-Deficient Mice"; PLOS ONE, 8:3, Mar. 2013, p. 1-10.

Cauli, Alberto et al.; "Current perspective on the role of the interleukin-23/interleukin-17 axis in inflammation and disease (chronic arthritis and psoriasis)"; Immuno Targets and Therapy, 4, 2015, p. 185-190.

Chan, Chi-Chao et al.; "Molecular Pathology of Macrophages and Interleukin-17 in Age-Related Macular Degeneration"; Advances in Experimental Medicine and Biology, 801: 2014; p. 193-198.

Chehimi, Marwa et al.; "Pathogenic Role of IL-17-Producing Immune Cells in Obesity, and Related Inflammatory Diseases"; Journal of Clinical Medicine, 6:68, 2017, p. 1-19.

Coimbra, S et al "Interleukin (IL)-22 IL-17 IL-23 IL-8 vascular endothelial growth factor & tumour necrosis factor-α levels in patients with psoriasis before during & after psoralen-ultraviolet A & narrowband ultraviolet B therapy" BJD:163, 2010, 1282-90.

Di Cesare, Antonella et al.; "A Role for Th17 Cells in the Immunopathogenesis of Atopic Dermatitis?"; Journal of Investigative Dermatology, 128:2008, p. 2569-2571.

Gaffen, Sarah L. et al.; "IL-23-IL-17 immune axis: Discovery, Mechanistic Understanding; and Clinical Testing"; Nature Reviews Immunology, 14:9, Sep. 2014, p. 585-600.

Giuliani, Nicola et al.; "Novel Insights into the Role of Interleukin-27 and Interleukin-23 in Human Malignant and Normal Plasma Cells"; Clinical Cancer Research, 17:22, Nov. 15, 2011, p. 6963-6970.

Guttman-Yassky, Emma et al.; "Low Expression of the IL-23/Th17 Pathway in Atopic Dermatitis Compared to Psoriasis"; The Journal of Immunology, 181: 2008, p. 7420-7427.

Hasegawa, Eiichi et al.; "IL-23-Independent Induction of IL-17 from γ δT Cells and Innate Lymphoid Cells Promotes Experimental Intraoculat Neovascularization"; The Journal of Immunology; 190: 2013, p. 1776-1787.

Koga; Chizuko et al.; "Possible Pathogenic Role of Th17 Cells for Atopic Dermatitis"; Journal of Investigative Dermatology, 128:2008, p. 2625-2630.

Lemancewicz, Dorota et al.; "The role of Interleukin-17A and Interleukin-17E in multiple myeloma patients"; Medical Science Monitor, 18:1, 2012, p. BR54-BR59.

Leonardi, Salvatore et al.; "Serum interleukin 17, interleukin 23, and interleukin 10 values in children with atopic eczema/dermatitis syndrome (AEDS): Association with clinical severity and phenotype"; Allergy Asthma Proceedings, 36: 2015, p. 74-81.

Lin, Wan-Wan et al.; "A cytokine-mediated link between innate immunity, inflammation, and cancer"; The Journal of Clinical Investigation, 117:5, May 2007, p. 1175-1183.

Liu, Jian et al.; "Expression of IL-23R and IL-17 and the pathology and prognosis of urinary bladder carcinoma"; Oncology Letters, 16, 2018, p. 4325-4330.

Lockshin, Benjamin et al.; "Interleukin 17, inflammation, and cardiovascular risk in patients with psoriasis"; Journal of the American Academy of Dermatology, 79:2, Aug. 2018, p. 345-352.

Madhur, Meena S. et al.; "Role of Interleukin 17 in Inflammation, Atherosclerosis and Vascular Function in Apolipoprotein E-Deficient Mice"; Arteriosclerosis, Thrombosis, and Vasular Biology, Jul. 2011: 31(7), p. 1565-1572.

McAllister, Florencia et al.; "Th17 cytokines in non-melanoma skin cancer"; European Journal of Immunology, 45:3; Mar. 2015, p. 692-694.

Mudigonda, Parvathi et al.; "Interleukin-23 and interleukin-17: Importance in pathogenesis and therapy of psoriasis"; Dermatology Online Journal, 18:10, 2012, p. 1-16.

Nograles, Kristine E. et al.; "Atopic dermatitis (AD) keratinocytes exhibit normal Th17 cytokine responses"; Journal of Allergy and Clinical Immunology, 125:3, Mar. 2010, p. 744-746.

Park, Sung-Hyun et al.; "Interleukin 13- and interleukin 17A-induced pulmonary hypertension phenotype due to inhalation of antigen and fine particles from air pollution"; Pulmonary Circulation, 4:4, Dec. 2014, p. 654-668.

Pellegrini, Cristina et al.; "Expression of IL-23/Th17-related cytokines in basal cell carcinoma and in the response to medical treatments"; PLOS ONE: Aug. 22, 2017, p. 2-17.

Peng, Ling-Long et al.; "IL-23R mutation is associated with ulcerative colitis: A systemic review arid meta-analysis"; Oncotarget, 8:3, 2017, p. 4849-4863.

Prabhala, Rao H. et al.; "Elevated IL-17 produced by TH17 cells promotes myeloma cell growth and inhibits immune function in multiple myeloma"; Blood, 115:26, Jul. 1, 2010, p. 5385-5392.

Prabhala, Rao H. et al.; "Targeting IL-17A in Multiple Myeloma: A Potential Novel Therapeutic Approach in Myeloma"; Leukemia, 30:2, Feb. 2016, p. 379-389.

Qiu, Ao-Wang et al.; "Blocking IL-17A Alleviates Diabetic Retinopathy in Rodents"; Cellular Physiology and Biochemistry: 41, 2017, p. 960-972.

Shin; Jae Il et al.; "A role for IL-17 in age-related macular degeneration"; Nature Reviews: Immunology, 2013, p. 1.

Song, Qinglei et al.; "Expresssion of inflammatory cytokines in retina ischemia-reperfusion injury rats"; Biomedical Research, 28:7, 2017, p. 3066-3071.

Tang, Qiu et al.; "Hmgb 1-IL-23-IL-17-IL-6-Stat3 Axis Promotes Tumor Growth in Murine Models of Melanoma"; Mediators of Inflammation, V 2013; p. 1-13.

Teng, Michele W. L. et al.; "IL-23 suppresses innate immune response independently of IL-17A during carcinogenesis and metastasis"; PNAS, 107:18, May 4, 2010, p. 8328-8333.

Van der Fits, Leslie et al.; "Imiquimod-Induced Psoriasis-Like Skin Inflammation in Mice is Mediated via the IL-23/IL-17 Axis"; The Journal of Immunology, 182: 2009, p. 5836-5845.

Wang, K. et al.; "The IL-23 to IL-17 cascade inflammation-related cancers"; Clinical and Experimental Rheumatology, Oct. 2015, p. S-87-S-90.

Wang, Lin et al.; "IL-17 can promote tumor growth through an IL-6-Stat3 signaling pathway"; The Journal of Experimental Medicine, Jun. 2009, p. 1457-1464.

Whibley, Natasha et al.; "Gut-Busters: IL-17 Ain't Afraid of No IL-23"; Immunity, 43, Oct. 20, 2015, p. 620-622.

Yago, Toru et al.; "IL-23 and Th17 Disease in Inflammatory Arthritis"; Journal of Clinical Medicine, 6:81, 2017, p. 1-9.

Yen, David et al.; "IL-23 is essential for T cell-mediated colitis and promotes inflammation via IL-17 and IL-6"; The Journal of Clinical Investigation, 116:5, May 2006, p. 1310-1316.

Zhang, Jun et al.; "Th17 Cell-Mediated Neuroinflammation Is involved in Neurodegeneration of Aβ1-42-Induced Alzheimer's Disease Model Rats"; PLOS ONE, Oct. 4, 2013: https://doi.org/10.1371/journal.pone.0075786, p. 1-9.

Hu, Yuehua et al.; "Imbalance between IL-17 A-Producing Cells and Regulatory T Cells during Ischemic Stroke"; Mediators of Inflammation, vol. 2014, Article ID 813045, p. 1-8.

Liu, Yingsong et al.; "Correlation of IL-17 Level in Synovia and Severity of Knee Osteoarthritis"; Medical Science Monitor, 21, 2015, p. 1732-1736.

(56) References Cited

OTHER PUBLICATIONS

DeSelm, Carl J. et al.; "IL-17 Mediates Estrogen-deficient Osteoporosis in an Act1-dependent Manner"; Journal of Cellular Biochemistry, 113:9, Sep. 2012, p. 2895-2902.

Cheng, Gao et al.; "IL-17 Stimulates Migration of Carotid Artery Vascular Smooth Muscle Cells in an MMP-9 Dependent Manner via p38 MAPK and ERK1/2-Dependent NF-κB and AP-1 Activation"; Cellular and Molecular Neurobiology, 29; 2009, p. 1161-1168.

Abadja, Farida et al.; "Significance of Th17 Immunity in Transplantation"; Current Opinion in Organ Transplantation, 17:1, Feb. 2012, p. 8-14.

Sun, Xicai et al; "The presence of tumor-infiltrating IL-17-producing cells in juvenile nasopharyngeal angiofibroma tumor microenvironment is a poor prognostic factor"; American Journal of Otolaryngology—Head & Neck Medicine & Surgery, 35, 2014, p. 582-88.

Peiser, Matthias; "Role of Th17 Cells in Skin Inflammation of Allergic Contact Dermatits"; Clinical and Development Immunology, vol. 2013, Article ID 261037, 1-10 pages.

Shabgah, Arezoo Gowhari et al.; "Interleukin-17 in human inflammatory diseases"; Postępy Dermatoiogii i Alergologii, XXXI: 4, 2014, p. 256-261.

Boyd, T. et al.; "Interleukin-17 inhibition in psoriatic arthritis"; Clinical and Experimental Rheumatology, 2015, p. S-119-S-123.

\* cited by examiner

EFFECT OF IS181 ON PRO-APOPTOTIC CELLS
(TUNEL POSITIVE POPULATION)
AFTER 48 H OF TREATMENT

| SAMPLE | CONC. | % INCREASE IN TUNEL-POSITIVE CELL POPULATION WRT CONTROL (UNTREATED CELLS) |
|---|---|---|
| IS181 | 100μg/ml | −30.5 |
| | 500μg/ml | −2.6 |
| | 1000μg/ml | −53.1 |
| | 2000μg/ml | −40.1 |
| | 5000μg/ml | 28.3 |
| BA | 10μg/ml | 21.3 |
| | 20μg/ml | 48.2 |
| | 50μg/ml | 61.6 |
| CURCUMIN | 10μM | −72.2 |
| | 20μM | −76.1 |
| ANTHRALIN | 1μM | −87.0 |

Fig. 6

CAPSASE-3 ASSAY : CONCLUSION

| TEST CONCENTRATION | | PERCENTAGE INDUCTION OF CASPASE-3 ENZYME ACTIVATION WRT UNTREATED |
|---|---|---|
| UNTREATED | | 0.00 |
| ANTHRALIN-0.1μM | | 101.85 |
| IS 181 (μg/ml) | 100 | −20.37 |
| | 500 | 7.41 |
| | 1000 | 29.63 |
| | 2000 | 50.00 |
| | 5000 | COULDN'T BE TESTED DUE TO VERY LOW AMOUNT OF PROTEIN DUE TO NECROTIC CELL DEATH |

Fig. 7A

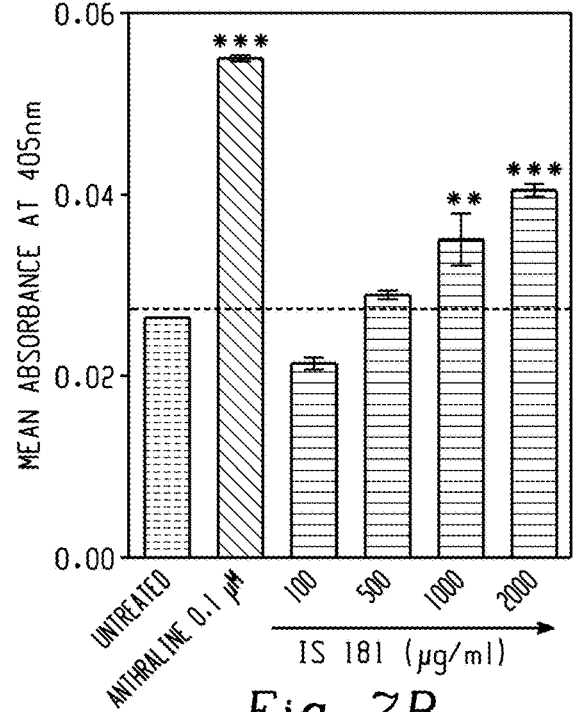

Fig. 7B

INHIBITION OF ENDOTHELIAL CELL PROLIFERATION: CONCLUSION

| TEST CONCENTRATION | | ABSORBANCE (MEAN ± SD) AT 5-10 nm | % INHIBITION OF FBS STIMULATED CELL GROWTH |
|---|---|---|---|
| DMEM ALONE | | 0.21 ± 0.004 | 60.31 |
| DMEM + 10% FBS | | 0.52 ± 0.015 | 0.00 |
| IS 181 (μg/ml) | 1 | 0.48 ± 0.006 | 7.47 |
| | 5 | 0.45 ± 0.027 | 14.38 |
| | 10 | 0.46 ± 0.012 | 12.38 |
| | 50 | 0.41 ± 0.011 | 21.89 |
| | 100 | 0.41 ± 0.012 | 21.00 |
| | 500 | 0.33 ± 0.004 | 36.76 |
| | 1000 | 0.22 ± 0.008 | 56.99 |
| | 2000 | 0.09 ± 0.003 | 83.33 |
| PACLITAXEL (nM) | 10 | 0.38 ± 0.012 | 27.57 |
| | 50 | 0.23 ± 0.008 | 56.92 |
| | 100 | 0.19 ± 0.006 | 62.73 |
| | 500 | 0.19 ± 0.003 | 70.07 |
| | 1000 | 0.06 ± 0.001 | 69.41 |
| ANTHRALIN (μM) | 0.01 | 0.48 ± 0.025 | 7.21 |
| | 0.1 | 0.45 ± 0.018 | 14.61 |
| | 0.5 | 0.42 ± 0.013 | 20.36 |

MATCH TO FIG. 9B

Fig. 9A

RESULTS

INHIBITION OF ENDOTHELIAL CELL MIGRATION: CONCLUSION

EFFECT OF IS 181 ON INHIBITION OF MIGRATION OF HUMAN ENDOTHELIAL (EA.HY.926) CELLS

| CONCENTRATIONS | | % INHIBITION OF MIGRATION WRT TO RESPECTIVE 0 H CONTROL |
|---|---|---|
| SFM | | 85 |
| FBS 10 | | 0 |
| PACLITAXEL (10 nM) | | 71 |
| IS 181 | 0.1 µg/ml | 0 |
| | 1 µg/ml | 0 |
| | 10 µg/ml | 17 |
| | 50 µg/ml | 34 |
| | 100 µg/ml | 41 |
| | 1 mg/ml | 54 |

INHIBITORY EFFECT OF IS 181 ON VEGF
SECRETION IN HACAT CELLS AFTER 24 H

| SAMPLES | | CONC. OF VEGF (pg/ml) | % INHIBITION OF VEGF WRT UNTREATED (BASAL) LEVELS |
|---|---|---|---|
| CONTROL (UNTREATED) | | 3592.7 | 0 |
| CUR 1 μM | | 3059.1 | 14.9 |
| RA 1 μM | | 2775.1* | 22.8 |
| RA 10 μM | | 2982.4 | 17.0 |
| IS 181 (μg/ml) | 0.1 | 2982.4 | 17.0 |
| | 1 | 3139.7 | 12.6 |
| | 5 | 3193.5 | 11.1 |
| | 10 | 3128.2 | 12.9 |
| | 100 | 3565.8 | 0.7 |

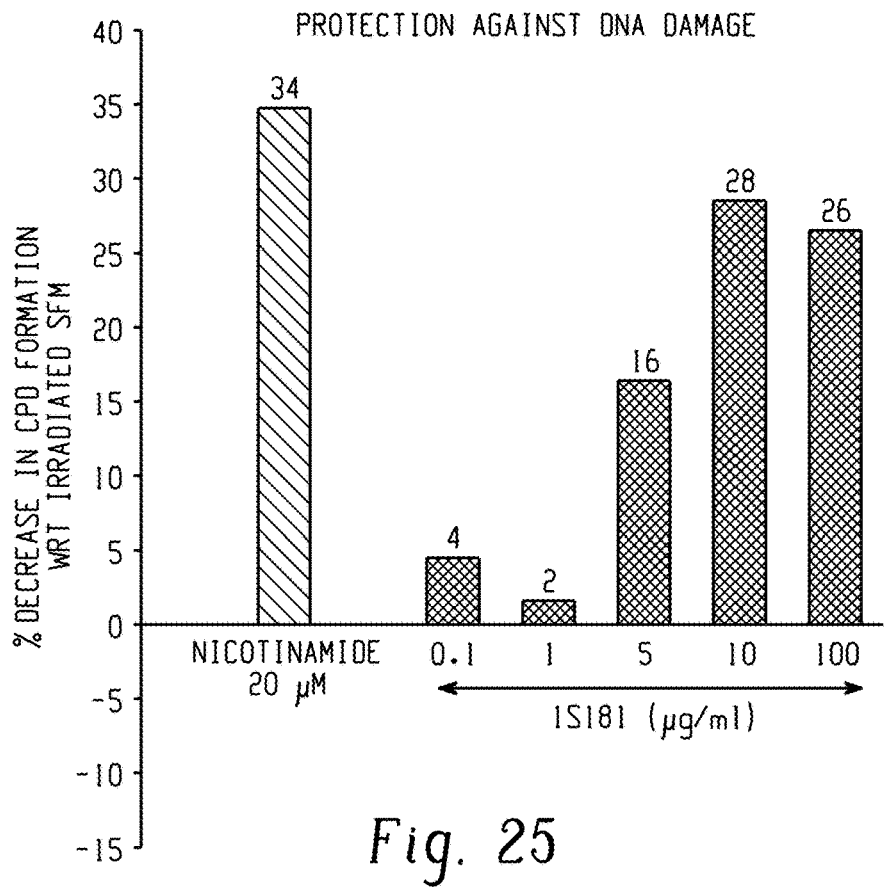
Fig. 25

Fig. 26

SEQUENCE LISTING

<160> NUMBER OF SEQ ID NOS: 1

<210> SEQ ID NO 1
<211> LENGTH: 11
<212> TYPE: PRT
<213> ORGANISM: murineI

<400> SEQUENCE: 1

Trp Val Gln Arg Val Val Glu Lys Phe Leu Lys
1               5                   10

PEPTIDE FOR TREATING INFLAMMATORY DISEASES

FIELD OF THE INVENTION

The present invention provides a peptide having anti-inflammatory activity. The present invention particularly provides a peptide for the treatment of diseases including inter alia tumors, arthritis, ischemic retinopathies, age-dependent macular degeneration, chronic transplant rejection, Psoriasis, Psoriatic Arthritis, Atherosclerosis, Restenosis, Obesity, pulmonary hypertension, chronic respiratory diseases, cerebral ischemia, dementia, vascular malformations, inflammatory bowel disease, osteoporosis/bone resorption, ulcerative colitis, respiratory distress syndrome, diabetes, atopic dermatitis, Actinic Keratosis, skin delayed type hypersensitivity disorders, Alzheimer's disease, multiple sclerosis, multiple myeloma. The present invention also provides the method of preparation of the peptide and compositions, and kits comprising the peptide. The invention further provides the method of treating inflammatory diseases employing the peptide of the present invention.

BACKGROUND OF THE INVENTION

Inflammatory diseases affect the majority of population world over. Inflammatory disease include (not limiting to) tumors, arthritis, ischemic retinopathies, age-dependent macular degeneration, chronic transplant rejection, Psoriasis, Atherosclerosis, Restenosis, Obesity, pulmonary hypertension, chronic respiratory diseases, cerebral ischemia, dementia, vascular malformations, inflammatory bowel disease, osteoporosis/bone resorption, ulcerative colitis, respiratory distress syndrome, diabetes, skin delayed type hypersensitivity disorders, Alzheimer's disease, multiple sclerosis.

Psoriasis is a noncontagious chronic inflammatory dermal disease affecting about 2% of the world population [M. P. Schon and W. H. Boehncke, New England Journal of Medicine, vol. 352, no. 18, pp. 1899-1912, 2005]. Psoriasis is a skin disease that affects a person's daily life on many levels including professional and social life. The physical and psychological impacts of psoriasis are comparable to those of cancer, heart disease, diabetes, or depression [Y. Liu, et al., Genes and Immunity, vol. 8, no. 1, pp. 1-12, 2007]. Psoriasis is characterized by recurrent red and scaly skin plaques that can be easily demarcated from adjacent normal skin [K. E. Nograles and J. G. Krueger, Experimental Cell Research, vol. 317, no. 9, pp. 1293-1300, 2011]. The percentage of the body affected by psoriatic plaques can vary. It is possible to observe mild (<2%), moderate (2-10%), and severe (>10%) psoriasis in different people [S. R. Rapp, et al., Journal of the American Academy of Dermatology, vol. 41, no. 3, pp. 401-407, 1999].

The cause of the disease is unknown, though it is believed to have a genetic component, and it has been suggested to be a T-cell mediated autoimmune skin disorder. There have been many attempts to treat the disease, and several topical and systemic treatments for psoriasis which inhibit cell division have been tried, with limited success in clearing the skin for short periods of time.

The histological characteristics of many dermal inflammatory diseases include: epidermal hyperplasia (abnormal differentiation and incomplete maturation of keratinocytes), a thickened epidermis, and a reduced or absent granular layer. Psoriasis is one such disease which has been long thought to be caused by hyperproliferation of keratinocytes. However, when immunomodulatory treatments became effective, the immune system was found to be an important factor in the development of the disease. Raychaudhuri, et al. proposed in 1986 a possible role for neuropeptides in the pathogenesis of psoriasis (Raychaudhuri, P., Farber, E. M. in Psoriasis 3rd ed. (pp. 383-391).

Psoriasis is an inflammatory disease in which dendritic cells, T lymphocytes, macrophages, neutrophils, and keratinocytes are responsible for the initiation of skin lesions. Presentation of antigen and the formation of the immunological synapse causes the secretion of various cytokines/chemokines and allows the differentiation of T cells into effector cells such as Th1, Th2, and Th17. Thus, each effector cell will secrete particular cytokines.

It has been shown that IFN-$\alpha$, TNF-$\alpha$, and IL-2 increase the proliferation of keratinocytes [C. E. Griffiths and J. N. Barker, The Lancet, vol. 370, no. 9583, pp. 263-271, 2007]. TNF-$\alpha$ activates the development of lesions by increasing the number of molecules involved in the inflammatory response or the adhesion molecules. Studies on inflammatory skin models suggest that IL-23 (a key cytokine that has been found to play a critical role in the pathogenesis of psoriasis) and Th17 T cells (which produce IL-17 and IL-22) may be pivotal inducers of epidermal hyperplasia and thus may modify epidermal differentiation in inflammatory diseases [Y. Zheng et al., Nature, vol. 445, no. 7128, pp. 648-651, 2007].

In addition to genetic predisposition, several in vivo studies have shown the involvement of T helper (Th) 17 cells as well as secretion of cytokines such as interleukins and TNF$\alpha$, by skin associated cells such as keratinocytes, dendritic and T helper cells, as key players in the development of the inflammatory response involved in the pathogenesis of psoriasis and other autoimmune inflammatory diseases. The secretion of cytokines such TNF$\alpha$ and Interleukin (IL)-23, which stimulates survival and proliferation of Th17 cells, also serves as a key master cytokine regulator for these diseases. (Fitch et al. (2007) Curr Rheumatol Rep. 9:461-7). Th17 cells within dermis in turn, induce secretion of IL-17A and IL-22. IL-22, in particular, derive keratinocyte hyperproliferation and augment the inflammatory response (Fitch et al. (2007) Curr Rheumatol Rep 9:461-7).

US20140220030 describes a method for the treatment and prevention of psoriasis by modulating the concentration of neuropeptide calcitonin gene-related peptide (CGRP) in the body, especially in the skin, e.g., by the use of CGRP antagonists. This invention is based on the notion that by changing the level of CGRP, at least in the psoriatic lesions, such as by blocking the activity of CGRP, the disease can be treated and/or prevented. This is effected by the administration of CGRP antagonist compounds, or by administering tryptase or other compounds affecting the level of CGRP. The results of this invention indicate that increased concentration in CGRP level in the skin is a very early event in the development of psoriasis. This supports that failure in regulating the GCRP level (i.e. an enhanced CGRP level) could be a causative factor in the psoriasis disease.

Although many studies have been performed on the possible causes of inflammatory diseases, the origin of the diseases such as psoriasis remains unknown. Currently, several treatments are available to help control psoriasis; however, the available treatments are only able to relieve the symptoms and lives of individuals [U. Mrowietz, et al., Archives of Dermatological Research, vol. 303, no. 1, pp. 1-10, 2011]. The choice of the most appropriate treatment depends on the patient's general health, age, comorbidities, form and severity of the pathology, and, also, on the affected body parts.

Although the treatments available for many inflammatory diseases have increased rapidly in recent years; however, they are still incomplete. For instance, although there are many drugs for different types of psoriasis, no drug can cure the disease. In addition, many of the drugs have serious side effects. Research has led to the development of new biological drugs that are produced through biotechnology which are effective for long-term. These biological treatments are an alternative to conventional treatments for moderate and severe psoriasis.

In recent years, findings on the immunologic factors related to the inflammatory diseases have changed the treatment of many of these diseases and created new biological drugs. These new classes of treatments consist in the fusion of proteins and monoclonal antibodies that specifically target the activity of T cells or inflammatory cytokines by inhibiting or modulating specific immune system factors. Biological drugs save other organs and minimize side effects.

For instance, US20140170138 relates to humanized anti-HSP65 derived peptide, specifically, peptide-6 antibodies and any antigen-binding fragments thereof. The invention relates to humanized anti-peptide-6 antibodies, compositions, methods and uses thereof for the treatment of immune-related disorders. The invention relates to a humanized antibody or any antigen-binding fragment thereof that specifically binds a polypeptide. The polypeptide known as peptide-6, is derived from HSP65.

US20130310309 provides a topical pharmaceutical composition for treating a skin disorder selected from the group consisting of Herpes viral infection, Varicella viral infection, rash, insect bites, jellyfish stings, burns, psoriasis, itching, skin allergic response, skin lesions as a result of drug or medical treatment side effects or complications, and hypopigmentation. The composition comprises a peptide of the formula pGLU-X-Y-Z, where X, Y and Z are amino acids, with or without an alkyl group, and a pharmaceutically acceptable excipient.

US20130296250 provides a method and kit for treatment of psoriasis using protein kinase C (PKC)-alpha inhibitors. Exemplary inhibitors include peptide PKC-alpha inhibitors which specifically inhibit PKC-alpha activity leading to the attenuation and treatment of psoriasis.

US20130210707 provides a peptide having antibacterial or anti-inflammatory activity and a pharmaceutical composition containing the same as an active ingredient, and more particularly to a peptide having antibacterial or anti-inflammatory activity against dental bacteria, including periodontal pathogens, and bacteria causing atopic dermatitis, and to a pharmaceutical composition containing the peptide as an active ingredient. The peptide having antibacterial or anti-inflammatory activity can be used for the treatment of both dental infectious diseases, including periodontitis or peri-implantitis, and inflammations, including atopy, psoriasis or arthritis.

However, these treatments have a high cost and significant side effects. Research continues to elucidate new pathological mechanisms and develop new proteins for treatment of inflammatory diseases such as psoriasis. These proteins participate in biological processes involved in the immune response to psoriasis and are found in all cells.

In addition, while psoriasis is considered a topical chronic skin disease, many of the existing effective drugs are systemic, which are based on immune suppression and as a result appear to lead to adverse effects, of which some can be severe. On the other hand, current topical treatments to psoriasis appear to be only moderately effective in reducing symptoms and overcoming pathology. This situation leads to the apparent practice that psoriasis patients commonly visit multiple doctors in a short period of time, indicating their dissatisfaction with available care. As a result, there is a strong need for an effective therapeutic alternative which targets multiple components of the disease's pathogenesis, while retaining a low level of side effects.

Accordingly the present invention provides a cost effective, non-toxic peptide having anti-inflammatory activity, and which is effective for the treatment of inflammatory disease such as.

BRIEF DESCRIPTION OF DRAWINGS

FIG. 6: Shows TUNEL assay results

FIGS. 7A-7B: Shows the results of the Caspase-3 Assay.

FIGS. 9A-9B: Effect of IS 181 on inhibition of endothelial cell proliferation.

FIG. 25: Protection against DNA damage by IS 181.

FIG. 26: Strategy followed for preformulation development and maximum feasible Concentration (MFC) determination of IS 181.

OBJECTS OF THE PRESENT INVENTION

Figure 1:
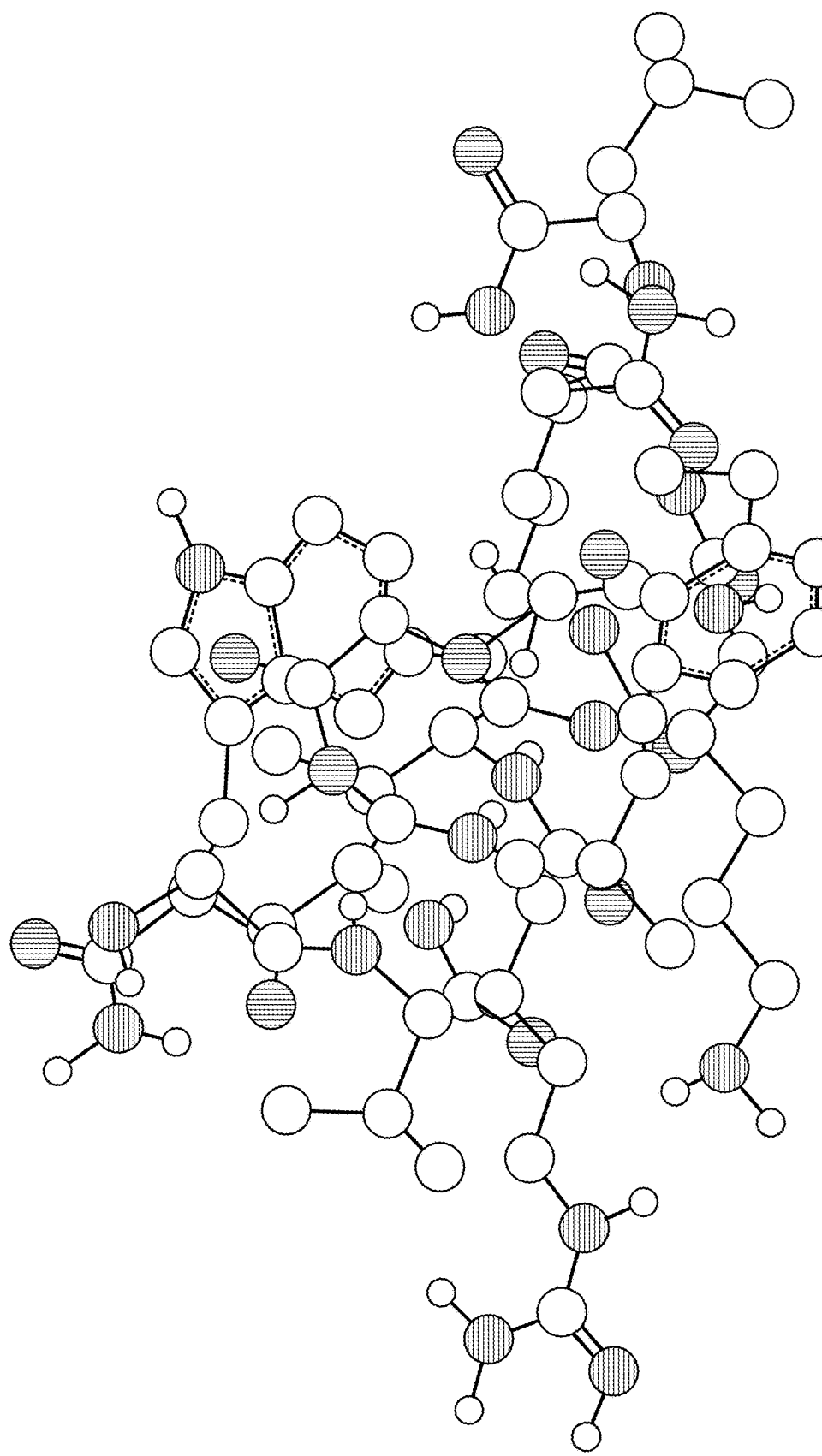
FIG. 1 shows the three dimensional structure of the peptide IS181.

It is an object of the present invention to provide a peptide having anti-inflammatory activity.

Another object of the present invention is to provide pharmaceutical compositions and kits containing the above peptide as an active ingredient.

Yet another object of the present invention is to provide a method of treatment of psoriasis employing the anti-inflammatory peptide.

Still another object of the present invention is to provide a method of preparing the peptide.

SUMMARY OF THE PRESENT INVENTION

To achieve the above objects, the present invention provides a peptide IS181 which has anti-inflammatory activity. The peptide of the present invention has SEQ ID NO. 1. The present invention also provides compositions for treating psoriasis which contains the above peptide as an active ingredient. The invention also provides a method of treating psoriasis in a subject. The method includes administering to the subject the peptide IS181 of SEQ ID No. 1 thereby treating psoriasis in the subject. The present invention provides a kit for treating psoriasis in a subject. In various embodiments, the kit includes the peptide and instructions for administering the peptide to the subject. The present invention also provides a method of preparing the peptide IS181.

The present invention provides a peptide with anti-inflammatory activity, the peptide having an amino acid sequence of SEQ ID NO: 1.

In another embodiment the present invention provides a peptide as claimed in claim 1 wherein the peptide has the chemical formula $C_{69}H_{110}N^{18}O_{15}$.

In yet another embodiment the peptide of the present invention inhibits Interferon gamma (IFN-γ), thymus and activation regulated chemokine, Interleukin-8, Thymic stromal lymphopoietin secretion.

In another embodiment the peptide of the present invention is for the treatment and/or prevention of tumors, rheumatoid arthritis, ischemic retinopathies, age-dependent macular degeneration, chronic transplant rejection, psoriasis, atherosclerosis, restenosis, obesity, pulmonary hypertension, chronic respiratory diseases, cerebral ischemia, dementia, vascular malformations, rheumatoid arthritis, inflammatory bowel disease, osteoarthritis, osteoporosis/bone resorption, ulcerative colitis, respiratory distress syndrome, diabetes, skin delayed type hypersensitivity disorders, Alzheimer's disease, multiple sclerosis, particularly psoriasis.

In another embodiment the peptide of the present invention is for monotherapy, in combination therapy, conjugate therapy and/or for delivery systems such as pegylation, liposomes, nanoemulsions.

In still another embodiment the present invention provides the method of preparing the peptide of SEQ ID No. 1 (Trp-Val-Gln-Arg-Val-Val-Glu-Lys-Phe-Leu-Lys) comprising: preparing peptydil resin containing the peptide of SEQ ID No. 1 (IS181) with resin; cleavage of the peptidyl resin cocktail to obtain crude peptide; purification of the crude peptide by HPLC to obtain pure peptide.

In yet another embodiment the present invention provides an anti-inflammatory composition containing the peptide as an active ingredient; and pharmaceutically acceptable carriers and excipients.

In another embodiment the present invention provides a wherein the peptide is in an amount of $10^{-3}$ to 1 part by weight, based on the total weight of the composition.

In still another embodiment the present invention provides a composition as wherein the peptide is preferably in an amount of $10^{-2}$ to $10^{-1}$ parts by weight, based on the total weight of the composition.

In yet another embodiment the present invention provides a composition wherein the pharmaceutically acceptable carriers and excipients are selected from the group consisting of excipients such as starch, lactose, calcium carbonate or calcium phosphate, binders such as starch, gum Arabia, carboxymethyl cellulose, hydroxymethyl cellulose or crystalline cellulose, lubricants such as magnesium stearate or talc, disintegrants such as calcium carboxymethylcellulose, talc or synthetic aluminum silicate, diluents such as water or vegetable oil, and mixtures thereof.

In another embodiment the present invention provides a composition further comprising active ingredients or amino acids which may act as Interferon gamma, thymus and activation regulated chemokine, Interleukin-8, thymic stromal lymphopoietin inhibitors or mixtures thereof.

In still another embodiment the present invention provides a kit comprising a composition comprising a peptide of SEQ ID No. 1 and pharmaceutically acceptable carriers and excipients.

In yet another embodiment the present invention provides a method of treating a subject infected with inflammatory diseases comprising administering the subject peptide of SEQ ID No. 1 or composition comprising the peptide of SEQ ID No. 1.

In still another embodiment the method of treating the subject in the present invention comprises administration selected from oral, subcutaneous, topical, intraperitoneal, intravenous or combination thereof.

DETAILED DESCRIPTION OF THE PRESENT INVENTION

Unless defined otherwise, all technical and scientific terms used herein have the same meaning as commonly understood by one of ordinary skill in the art to which the invention pertains. Generally, the nomenclature used herein and the experiment methods which are described hereinafter are those well-known and commonly employed in the art.

The present disclosure is based on the finding that a peptide IS181 is an effective peptide for treatment for inflammatory diseases.

The peptide has the sequence H-Trp-Val-Gln-Arg-Val-Val-Glu-Lys-Phe-Leu-Lys-OH (SEQ ID No. 1). FIG. 1 shows the three dimensional structure of the peptide IS181 (hereinafter also referred to as peptide of SEQ ID No. 1). The chemical structure and details of the peptide is provided herein:

The peptide of SEQ ID No. 1 exhibited inhibition of thymus and activation regulated chemokine (TARC) secretion by a maximum of 28.6% at 0.1 µg/ml as compared to TNF-α stimulated cells.

IS181 demonstrated inhibition of IL-8 secretion by a maximum of 19.8% at 1 µg/ml, as compared to LPS+PMA stimulated cells.

IS181 demonstrated Thymic stromal lymphopoietin (TSLP) inhibition at all the concentrations tested. In the concentration range of 0.1 µg/ml-100 µg/ml, secretion of TSLP was inhibited by 46.4%-53.6% as compared to LPS+PMA stimulated cells.

The peptide of SEQ ID No. 1 (IS181) has therapeutic potential for the treatment of melanoma, psoriasis and atopic dermatitis. IS181 exhibits anti-inflammatory activity in macrophages thereby suggesting therapeutic efficacy in inflammatory disorders such as Rheumatoid arthritis (RA).

The peptidyl resin containing the peptide of SEQ ID No. 1 (IS181) with resin is prepared by placing the resin in reaction vessel of the synthesizer and swelling with DMF; washing the resin with DMF; deprotecting by adding 20% piperidine in DMF to the resin and stirring and draining; weighing Fmoc Tyr (Fluorenylmethyloxycarbonyl tyrosine), HOBT and solubilizing in DMF to obtain a solution; adding DIC N,N'-Diisopropylcarbodiimide to the solution just before adding to the resin; mixing and checking for free amino group by a ninhydrin test. Formation of clear beads shows that the reaction is complete. The process is repeated with next amino acid sequence to obtain peptidyl resin (Resin with Peptide)

Thereafter cleavage cocktail is added to Peptidyl resin in round bottom flask and the mixture is swirled to obtain a solution. The solution is filtered through G4 sintered funnel

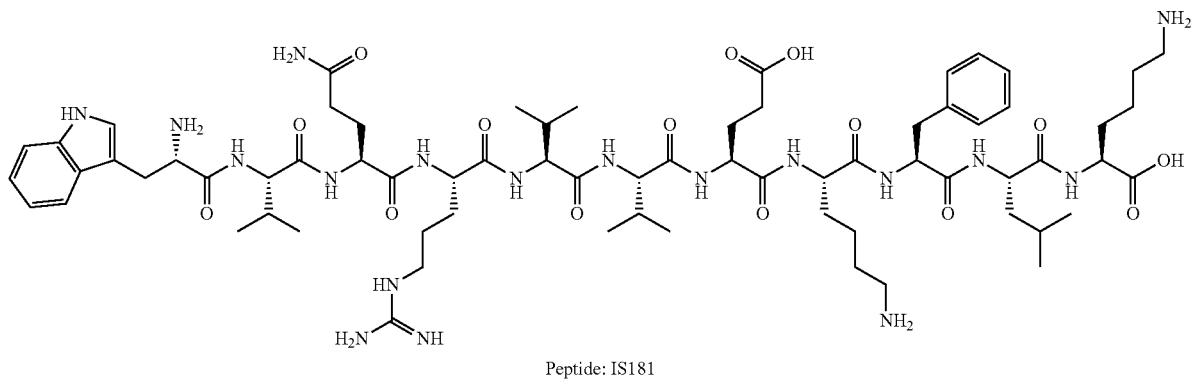 [SMILES: CC(C)C[C@H](NC(=O)[C@H](Cc1ccccc1)NC(=O)[C@H](CCCCN)NC(=O)[C@H](CCC(=O)O)NC(=O)[C@@H](NC(=O)[C@@H](NC(=O)[C@H](CCCNC(=N)N)NC(=O)[C@H](CCC(N)=O)NC(=O)[C@@H](NC(=O)[C@@H](N)Cc1c[nH]c2ccccc12)C(C)C)C(C)C)C(C)C)C(=O)N[C@@H](CCCCN)C(=O)O]

Peptide: IS181

Chemical Formula: $C_{69}H_{110}N_{18}O_{15}$

Exact Mass: 1430.840

Molecular Weight: 1431.723 m/z: 1430.840 (100.0%), 1431.843 (74.6%), 1432.847 (27.9%), 1433.850 (6.7%), 1431.837 (6.6%), 1432.840 (5.0%), 1432.844 (3.1%), 1433.847 (2.3%), 1433.844 (1.8%), 1431.846 (1.3%), 1434.853 (1.2%)

Elemental Analysis: C, 57.88; H, 7.74; N, 17.61; 0, 16.76

Peptide of SEQ ID No. 1 demonstrated inhibition of Interferon gamma (IFN-γ) secretion at various concentrations. In the concentrations range of 0.1 µg/ml-100 IFN-γ secretion was downregulated by 27.1%-40.1% as compared to TNF-α stimulated cells.

and the resin is washed with trifluoroacetic acid (TFA). The filtrates are collected and evaporated roto evaporator to remove TFA. The filtrate is precipitated with chilled diethyl ether. The round bottom flask is swirled for few minutes and kept in the deep freezer at −10 centigrade for over night. The crude peptide is obtained by centrifugation and air drying overnight. Pre-purification is performed by HPLC comprising: Collecting the fractions of the main peak of the peptide from the fraction collector and collecting all the fractions of the pure compounds which are greater than 90% purity; roto evaporating the collected fractions using roto evaporator to remove ACB (acetonitrile), thereafter lyophilisation is performed wherein the roto evaporated solution is loaded into the S.S. trays and lyophilized; the pure peptide is unloaded and weighed; purity test is performed by HPLC and Mass by LCMS and the pure peptide is stored at t −20° C. for further use.

Testing Procedure
Method:
Mobile Phase A—0.1% TFA in Water
Mobile Phase B—0.1% TFA in ACN
Injection volume—3 μl
Wave length—215 nm
Flow—1.0 ml/min
Column—Kromosil C18 [4.6 mm (i.d)×150 mm (length)×5 microns]
Run time—30 min
Purity NLT 98.0%

Figure 2:
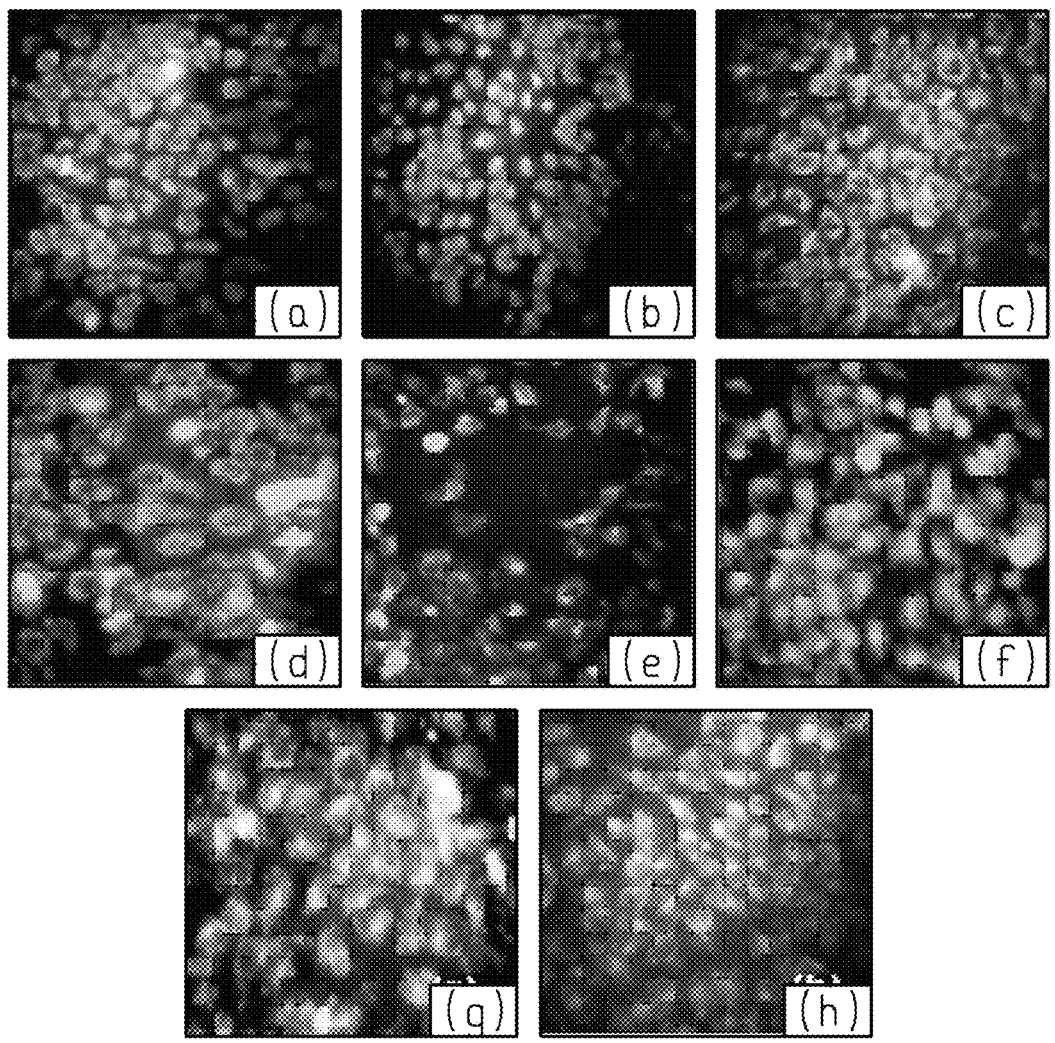
FIG. 2 shows the qualitative effect on mitochondrial membrane potential in HaCaT cells after 20 h of treatment. JC-1 images (10× magnification) of HaCaT cells: (a) & (b): Untreated; (c) & (d): Cells treated with 750 µg/ml of IS181; (e) & (f): Cells treated with 1 mg/ml of IS181; (g) & (h): Cells treated with 2 mg/ml of IS181
Figure 3:
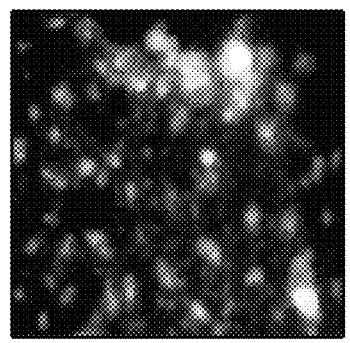
FIG. 3: JC-1 images (10× magnification) of HaCaT cells treated with 0.1% Triton X-100 (positive control)

FIG. 2 shows the qualitative effect on mitochondrial membrane potential in HaCaT cells after 20 h of treatment. JC-1 images (10× magnification) of HaCaT cells: (a) & (b): Untreated; (c) & (d): Cells treated with 750 μg/ml of IS181; (e) & (f): Cells treated with 1 mg/ml of IS181; (g) & (h): Cells treated with 2 mg/ml of IS181. FIG. 3 shows JC-1 images (10× magnification) of HaCaT cells treated with 0.1% Triton X-100 (positive control). It is evident from photomicrographs that an increase in green fluorescence was observed at concentrations ranging from 750 μg/ml to 2 mg/ml. Hence, considerable decrease in mitochondrial membrane potential was recorded. 34% to 88.6% decrease in mitochondrial membrane potential as compared to untreated cells was observed at concentrations ranging from 750 μg/ml to 2 mg/ml. Considerable increase in LDH release was recorded. ≥90% increase in LDH enzyme activity with respect to untreated was observed at concentrations ranging from 750 μg/ml to 2 mg/ml. The pattern observed is indicative of secondary necrosis.

The present invention provides treatment of inflammatory diseases such as psoriasis by administering to a subject an inhibitor of PKCα. The peptide of the present invention affects multiple components of psoriasis by 1) attenuating the inflammatory process in psoriatic plaques; and 2) controlling epidermal scaling in the plaques. Accordingly, in one aspect, the present disclosure provides a method of treating psoriasis in a subject. The method includes administering to the subject the peptide IS181 of SEQ ID NO. 1, thereby, treating psoriasis in the subject.

It is to be understood that the disclosure is not limited to particular compositions, methods, and experimental conditions described, as such methods and conditions may vary. It is also to be understood that the terminology used herein is for purposes of describing particular embodiments only, and is not intended to be limiting.

The principles and operation of the methods according to the present disclosure may be better understood with reference to the figures and examples described hereinafter. Unless defined otherwise, all technical and scientific terms used herein have the same meaning as commonly understood by one of skill in the art to which this disclosure belongs. Although any methods and materials similar or equivalent to those described herein can be used in the practice or testing of the disclosure, some preferred methods and materials are now described.

As used herein, the term "subject" refers to a mammalian subject. As such, treatment of psoriasis of any animal in the order mammalian is envisioned. Such animals include, but are not limited to horses, cats, dogs, rabbits, mice, goats, sheep, non-human primates and humans. Thus, the method of the present disclosure is contemplated for use in veterinary applications as well as human use.

The peptide of SEQ ID No. 1 according to the present invention may be a composition for treating inflammatory diseases. Herein, the inflammatory diseases may be selected from the group consisting of tumors, rheumatoid arthritis, ischemic retinopathies, age-dependent macular degeneration, chronic transplant rejection, psoriasis, atherosclerosis, restenosis, obesity, pulmonary hypertension, chronic respiratory diseases, cerebral ischemia, dementia, vascular malformations, rheumatoid arthritis, inflammatory bowel disease, osteoarthritis, osteoporosis/bone resorption, ulcerative colitis, respiratory distress syndrome, diabetes, skin delayed type hypersensitivity disorders, Alzheimer's disease, multiple sclerosis, particular psoriasis.

In the present invention, the composition for treating inflammatory infectious diseases may contain the peptide of SEQ ID No. 1 in an amount of $10^{-3}$ to 1 part by weight, and preferably $10^{-2}$ to $10^{-1}$ parts by weight, based on the total weight of the composition.

In the present invention, the composition for treating inflammatory diseases may contain a pharmaceutically acceptable carrier which is selected from the group consisting of excipients such as starch, lactose, calcium carbonate or calcium phosphate, binders such as starch, gum Arabia, carboxymethyl cellulose, hydroxymethyl cellulose or crystalline cellulose, lubricants such as magnesium stearate or talc, disintegrants such as calcium carboxymethylcellulose, talc or synthetic aluminum silicate, diluents such as water or vegetable oil, and mixtures thereof.

The peptide of SEQ ID No. 1 of the present invention may be employed in various pharmaceutical dosage forms. The anti-inflammatory composition of the present invention may be formulated in the form of powders, fine granules, liquids, sprays, ointments and gels, but is not limited thereto. The peptide may be formulated as lotion, cream, ointments, emulsions, foundations, oils, packs, soaps (including medicinal soap), body soaps, lipsticks, cosmetic, perfume, facial washes, mouth washes, bath products, hair tonics, and the like.

The peptide may be used in monotherapy or/and in combination therapy and may be employed in delivery systems such as pegylation, liposomes, nanoemulsions etc. The peptide may also be employed in conjugate therapy.

Those in need of treatment include those already with inflammatory diseases as well as those in which the disease is to be prevented. Hence, the subject may have been diagnosed as having inflammatory disease(s) or may be predisposed or susceptible to inflammatory disease(s).

Although the present invention has been described in detail with reference to the specific features, it will be apparent to those skilled in the art that this description is only for a preferred embodiment and does not limit the scope of the present invention. It will be obvious to those skilled in the art to make various changes, modifications and alterations to the invention described herein. To the extent that these various changes, modifications and alterations do not depart from the scope of the present invention, they are intended to be encompassed therein.

EXAMPLES

Example 1: Cell Viability in HaCaT, SK-MEL-28 & PBMCs @ 24 h, 72 Post Treatment

Cell Lines/Cells: Human Keratinocytes (HaCaT); Human melanoma (SK-MEL-28); Human PBMCs. Test Item: IS181 Treatment regimen: Single addition—24 h, #Multiple additions (3)–72 h; Concentration range: 1 ng/ml-2 mg/ml (triplicate wells); Sera Condition: Cell viability was assessed at two sera conditions: 1) Medium containing 1% FBS and 2)*Medium containing 10% FBS. Method of estimation: MTT assay. Criterion for Cytotoxicity: >30% loss of cell viability with respect to control cells. Positive control: Triton-X-100, Doxorubicin Hydrochloride.

TABLE 1

| | % Cytotoxicity | | | | | |
|---|---|---|---|---|---|---|
| | HaCaT (medium containing 1% FBS) | | SK-MEL-28 | | PBMCs | |
| Concentration (µg/ml) | 24 h | 72 h | 24 h | 72 h | 24 h | 72 h |
| 0.001 | — | — | −4.04 | — | — | — |
| 0.01 | — | — | −1.91 | — | — | — |
| 0.05 | — | — | 2.39 | — | — | — |
| 0.1 | −1.40 | −56.18 | −4.93 | −10.90 | — | — |
| 0.5 | −4.61 | −75.39 | −1.29 | −14.19 | — | — |
| 1 | 4.88** | −66.06 | −12.54 | −20.02 | — | — |
| 5 | 8.43*** | −37.48 | −16.34 | 9.03* | — | — |
| 10 | 5.75** | −44.45 | −14.00 | 6.16 | −76.48 | 18.71*** |
| 50 | 1.79 | −33.03 | −6.96 | −4.36 | −67.07 | 20.13*** |
| 100 | −0.58 | −42.45 | −2.97 | 5.78 | −88.33 | 14.00* |
| 500 | 18.92*** | 58.49*** | — | 94.02*** | #−105.40 | 32.71*** |
| 1000 | 87.80*** | 90.98*** | −11.87 | 90.95*** | 40.24 | 70.79*** |
| 2000 | 91.35*** | 89.38*** | — | 91.95*** | 52.96 | 66.08*** |

Each value represents the mean of triplicate wells; Statistical comparison with untreated was conducted using two-way analysis of variance (ANOVA) with Bonferroni post-tests (Graphpad prism software version 4),[2].
***represents significant difference with $p < 0.001$;
**represents significant difference with $p < 0.01$;
*represents significant difference with $p < 0.05$ The results of the cell viability test show that: (a) at 24 h, the peptide of SEQ ID NO. 1 demonstrated good extent of cytotoxicity (87%-91%) at concentrations 2 mg/ml in HaCaT cells; whereas no cytotoxic effects were recorded in SK-MEL-28 cells after 24 h of treatment; (b) At 72 h, IS181 demonstrated good extent of cytotoxicity at concentrations ≥0.5 mg/ml in HaCaT (58%-90%) and SK-MEL-28 (>90%) cells; (c) In PBMCs, 40% to 53% cytotoxicity was observed at concentrations 1 mg/ml after 24 h of treatment. Whereas at 72 h, IS181 demonstrated 33% to 66% cytotoxicity at concentrations >0.5 mg/ml Example 2: IC50 in HaCaT (Human Keratinocyte), SK-MEL-28 & PBMCs @ 24 h and 72 h Post Treatment with IS 181

In HaCaT cells, the IC50 values of 0.67 mg/ml and 0.42 mg/ml were obtained at 24 h and 72 h of treatment respectively. In Sk-MEL-28 cells, the IC50 value of 0.23 mg/ml was obtained at 72 h of treatment. In PBMCs, the IC50 values of 2 mg/ml and 0.98 mg/ml were obtained at 24 h and 72 h of treatment respectively.

TABLE 2

| IC50 value (test Item: IS 181 or Peptide of SEQ ID No. 1) | | | | | |
|---|---|---|---|---|---|
| HaCaT | | SK-MEL-28 | | PBMCs | |
| mg/ml | mM | mg/ml | mM | mg/ml | mM |
| 24 h | 0.67 | 0.47 | >1 | >0.7 | 2 | 1.4 |
| 72 h | 0.42 | 0.29 | 0.23 | 0.16 | 0.98 | 0.68 |

Example 3: SI (Selectivity Index) in HaCaT & SK-MEL-28 with Respect to PBMCs @ 24 h and 72 h Post Treatment Positive controls: Doxorubicin hydrochloride and Triton X 100. SI values of 3 and 2 were recorded in HaCaT cells after 24 h and 72 h of treatment respectively. SI value of 4 was recorded in SK-MEL-28 cells after 72 h of treatment

TABLE 3

| Selectivity Index -$IC_{50}$ (PBMC)/$IC_{50}$ (HaCaT/SK-MEL-28 cells) | | |
|---|---|---|
| | HaCaT | SK-MEL-28 |
| 24 h | 3 | ≤2 |
| 72 h | 2 | 4 |

At 24 h, IS181 demonstrated selective cytotoxic activity against human keratinocytes.

Example 4: Annexin-V Assay

Figure 4:
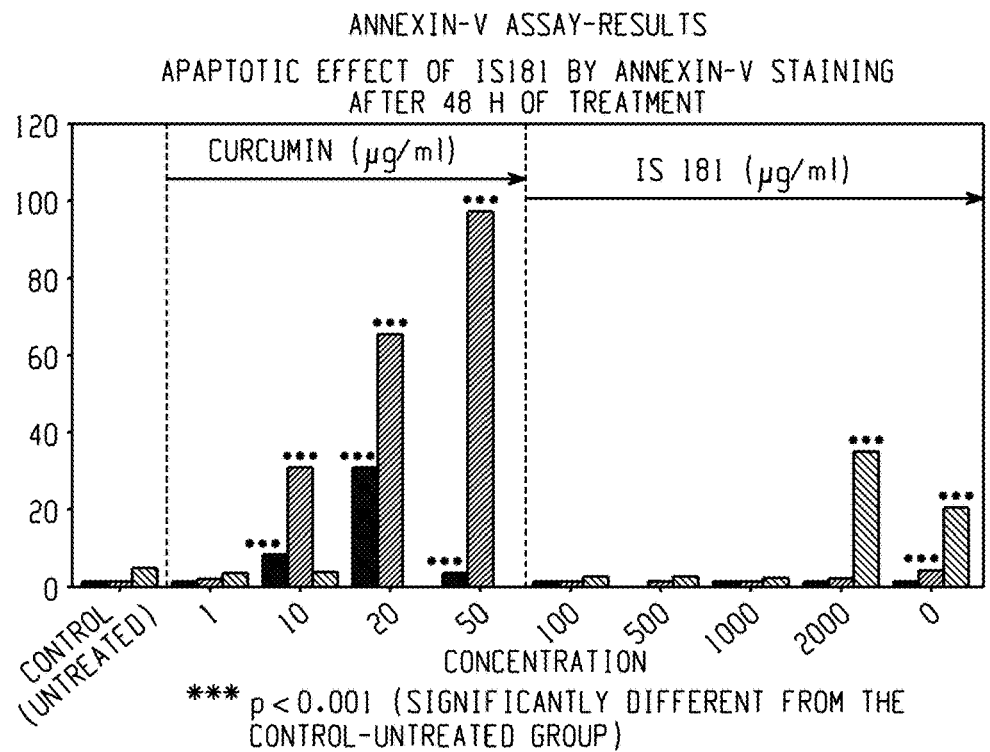
FIG. 4: Apoptotic effect of IS181 by Annexin-V staining after 48 h of treatment

Cell lines: Human Keratinocytes (HaCaT); test Item (TI): IS181; Treatment regimen: treated twice (once after 24 hours)-48 hours; concentration range: 100 6 g/ml-5000 6 g/ml.
Method:
HaCaT cells were plated in medium containing 10% FBS for 24 h; (b) cells were sera starved in 0.1% FBS for 3 hours; (c) cells were treated with IS181 for 24 hours; (d) after 24 hours, cells were again treated with IS181 for 24 hours; (e) after 48 hours of first treatment, cells were stained with Annexin-V reagent and acquired on flow cytometer; (f) fold increase in apoptotic cells (early and late apoptotic) and necrotic cells was calculated with respect to untreated control cells. Positive control: Curcumin. IS181 demonstrated an increase in early apoptotic cells by 2.3 fold at highest concentration of 5000 µg/ml, when compared with control (untreated) cells. IS181 demonstrated an increase in late apoptotic cells by 2.1 and 5.3 fold at concentrations of 2000 µg/ml and 5000 µg/ml. respectively, when compared with control (untreated) cells.•IS181 demonstrated an increase in necrotic cells by 7.9 and 4.5 fold at concentrations of 2000 µg/ml and 5000 µg/ml respectively, when compared with control (untreated) cells. Positive control (Curcumin) resulted in an increase in early apoptotic cells by 12.8-152.5 fold and late apoptotic cells by 2.4-138.4 fold respectively in the concentration range of 10 µM-50 µM. (FIG. 4)

Example 5: Cell Cycle Assay—Study Design

Figure 5:
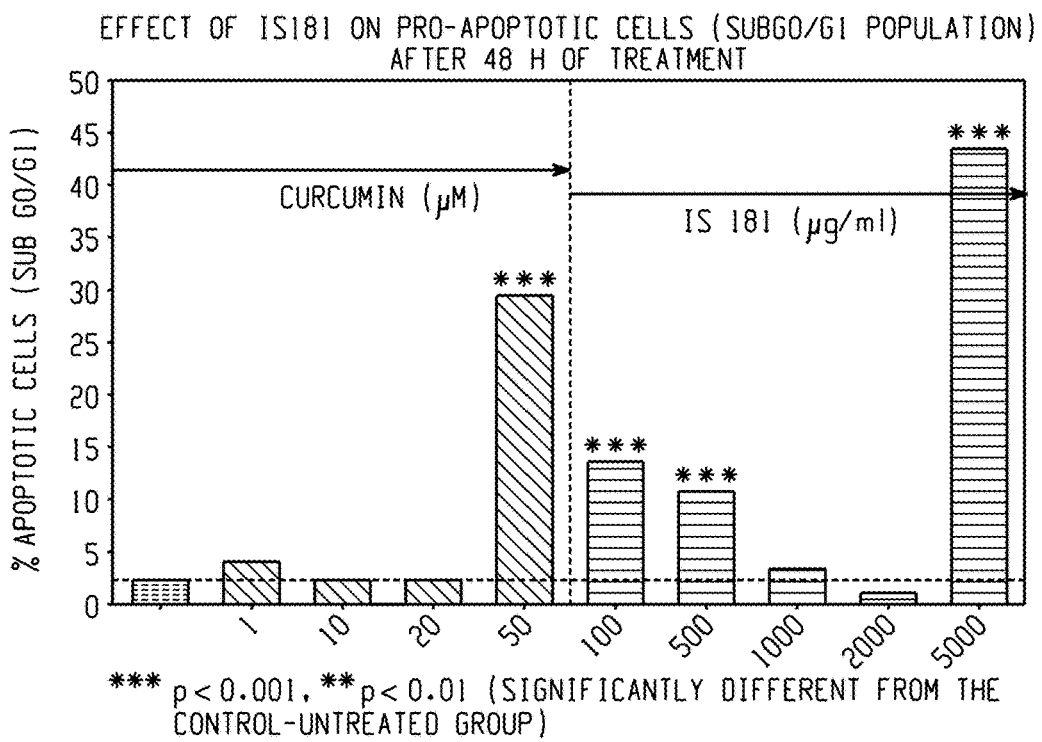
FIG. 5: Effect of IS181 on pro-apoptotic cells (SubG0/G1 population) after 48 hours of treatment.

Cell lines: Human Keratinocytes (HaCaT); test Item: IS181; treatment regimen: treated twice (once after 24 hours)-48 hours; concentration range: 100 6 g/ml-5000 6 g/ml. HaCaT cells were plated in medium containing 10% FBS for 24 hours. Cells were sera starved in 0.1% FBS for 24 hours. Cells were treated with IS181 for 24 hours. After 24 h, cells were again treated with IS181 for 24 hours. After 48 h of first treatment, cells were harvested and fixed in ethanol overnight. Cells were washed and stained with Cell cycle reagent and acquired on flow cytometer. Fold increase in pro-apoptotic cells [Sub(G0/G1)] was calculated with respect to untreated control cells. Positive control: Curcumin. IS 181 demonstrated an increase in pro-apoptotic cells (Sub-G0/G1 population) by 9.1 fold, 7.1 fold, 2.3 fold and 29.7 fold at 100 µg/ml, 500 µg/ml, 1000 µg/ml and 5000 µg/ml respectively as compared to control (untreated) levels. Positive control (Curcumin) resulted in an increase in pro-apoptotic cells (Sub-G0/G1 population) by 1.1 fold-19.9 fold as compared to control (untreated) levels in the concentration range of 1 µM-50 µM (FIG. 5).

Example 6: Tunel Assay

Cell lines: Human Keratinocytes (HaCaT); test item (TI): IS181; treatment regimen: treated twice (once after 24 hours)-48 hours; Concentration range: 100 6 g/ml-5000 6 g/ml. HaCaT cells were plated in medium containing 10% FBS for 24 hours. Cells were sera starved in 1% FBS for 24 hours. Cells were treated with IS181 for 24 hours. After 24 h, cells were again treated with IS181 for 24 hours. After 48 h of first treatment, cells were processed for TUNEL staining. Fold increase in apoptotic cells [TUNEL positive] was calculated with respect to untreated control cells. Positive control: Curcumin, Anthralin, Betullinic acid. IS 181 demonstrated an increase in apoptotic cells (TUNEL positive population) by 28.3% as compared to control (untreated cells) at the highest concentration tested; 5000 µg/ml. No increase in TUNEL positive cells was observed from 100 µg/ml-2000 µg/ml. Betullinic acid (Positive control) demonstrated increase in apoptotic cells (TUNEL positive population) by 21.3%, 48.2% and 61.6% in the concentration range of 10 µg/ml-50 µg/ml as compared to control (untreated cells) (FIG. 6).

In the examples provided herein the effect of positive controls is that at 24 h, Doxorubicin hydrochloride and Triton X 100 respectively demonstrated up to 48% and >90% cytotoxicity in HaCaT and SK-MEL-28 cells. At 72 h, Doxorubicin hydrochloride and Triton X 100 demonstrated >88% cytotoxicity in HaCaT cells. In SK-MEL-28 cells Doxorubicin hydrochloride and Triton X-100 respectively demonstrated up to 40% and >90% cytotoxicity. In PBMCs, Triton X 100 demonstrated 70% to 77% cytotoxicity at both the time points tested.

For testing Apoptosis the Human Keratinocytes (HaCaT) cell line has been employed. The growth conditions are DMEM containing 1% FBS. The test concentration range is IS181 is tested at concentrations around its IC50 value (for Quantitative analysis) 0.4-2 mg/ml. Test concentration range is IS181 is tested at the highest (Qualitative analysis) effective concentrations selected on the basis of Quantitative JC-1 assay. The method of estimation is Mitochondrial membrane depolarization by JC-1 assay (Early apoptosis), LDH enzyme release (Necrosis). Treatment regimen & time points are JC-1 assay—Single addition, 20 h; LDH assay—Single addition, 24 h; Positive control: Triton-X-100, Doxorubicin-hydrochloride Example 7: Mitochondrial Membrane Potential Assay or Mitochondrial Depolarization by JC-1 Assay Quantitative effect on $\Delta\psi m$ (Red fluorescence/Green fluorescence) in HaCaT cells post 20 hours of treatment. Test System: HaCaT (Human keratinocyte) cell line; Test item: IS 181; Treatment regimen: Single addition—20 hours; Concentration range: 400 µg/ml-2000 µg/ml; Sera Condition: Medium containing 1% FBS. Evaluation (Qualitative and quantitative) of differential JC-1 staining in treated cells after 20 h on incubation with the test peptides. End-point: Quantitative red fluorescence at 530 nm (excitation)/590 nm(emission); Quantitative green fluorescence at 485 nm (excitation)/528 nm (emission); Decrease in Red fluorescence/Green fluorescence ratio in treated cells with respect to untreated control; Photomicrographs (Qualitative data) of untreated and treated cells at effective doses (as obtained from quantitative analysis). IS 181 was tested for pro-apoptotic effects at concentrations around IC-50 values. _JC-1 assay was conducted in HaCaT cells treated with IS 181 for 20 hours. IS 181 demonstrated pro-apoptotic potential and led to 34% to 88.6% decrease in R/G ratio as compared to untreated cells (FIG. 3 and Tables-4 and 5 below).

TABLE 4

Mitochondrial membrane potential ($\Delta\psi m$)

| Concentration (µg/ml) | Red fluorescence intensity (RFU) | Green fluorescence intensity (RFU) | Red fluorescence intensity/Green fluorescence intensity |
|---|---|---|---|
| Untreated | 144.33 ± 9.43 | 13.33 ± 1.41 | 10.83 |
| 400 | 134.33 ± 32.06 | 13.67 ± 1.89 | 9.83 |
| 475 | 150.67 ± 11.31 | 14.83 ± 3.54 | 10.16 |
| 500 | 152.83 ± 31.82 | 14.5 ± 2.12 | 10.54 |
| 750 | 126.17 ± 6.36 | 17.67 ± 4.24 | 7.14 |
| 1000 | #102.25 ± 4.60 | #25.83 ± 5.42 | 3.96 |
| 2000 | #50.58 ± 0.12 | #41.25 ± 15.20 | **1.23 |

Each value represents the mean ± SD of two experiments, each conducted in triplicate wells;
Outliers within the replicates were removed to attain percent CV value <20%;
Statistical comparison with untreated was conducted using two - way analysis of variance (ANOVA) with Bonferroni post-tests (Graphpad prism software version 4;
**represents significant difference with $p < 0.01$

TABLE 5

Effect of positive controls
Mitochondrial membrane potential ($\Delta\psi m$)

| Test Concentration | Red fluorescence intensity (RFU) | Green fluorescence intensity (RFU) | Red fluorescence intensity/Green fluorescence intensity |
|---|---|---|---|
| Doxorubicin | | | |
| Untreated | 133.5 ± 28.99 | 13.67 ± 0.94 | 9.77 |
| 0.1 µM | #106.17 ± 15.32 | 11.5 ± 0.71 | 9.23 |

TABLE 5-continued

Effect of positive controls
Mitochondrial membrane potential (Δψm)

| Test Concentration | Red fluorescence intensity (RFU) | Green fluorescence intensity (RFU) | Red fluorescence intensity/Green fluorescence intensity |
|---|---|---|---|
| 1 µM | 93.25 ± 22.98 | 11.5 ± 0.71 | 8.11 |
| 10 µM | 49.83 ± 1.65 | 9.83 ± 4.48 | 5.07 |
| Triton X-100 | | | |
| Untreated | 133.5 ± 28.99 | 13.67 ± 0.94 | 9.77 |
| #0.01% | 33.25 ± 32.17 | 20.5 ± 17.68 | *1.62 |
| ##0.1% | 16.33 | 22.33 | *0.73 |

Each value represents the mean ± SD of two experiments, each conducted in triplicate wells;
Outliers within the replicates were removed to attain percent CV value <20%;
Each value represents the mean of triplicate wells;
Statistical comparison with untreated was conducted using two - way analysis of variance (ANOVA) with Bonferroni post-tests (Graphpad prism software version 4;
** represents significant difference with $p < 0.05$

Example 8: Caspase-3 Assay

Cell lines: Human Keratinocytes (HaCaT); Test Item (TI): IS 181; Treatment regimen: Multiple additions (2)—48 hours; Concentration range: 100 µg/ml to 5000 µg/ml (Duplicate wells); Sera Condition: Medium containing 1% FBS. HaCaT cells were plated in medium containing 10% FBS. The cells were then subjected to serum starvation in 1% FBS. Cells were treated with IS 181 for 48 h (retreatment was given after 24 hence two additions). Cells were lysed and protein was estimated. The above lysates were processed further for Caspase-3 enzyme activity assay using colorimetric based method. Percentage induction of Caspase-3 enzyme activation with respect to untreated; Positive control: Anthralin. IS 181 led to induction of Caspase-3 enzyme activation in HaCaT cells at all the concentrations tested except at 100 µg/ml. A maximum of 50% percent induction of Caspase-3 enzyme activation with respect to untreated was observed at 2000 µg/ml of IS 181 after 48 h of treatment. (FIGS. 7A-7B)

TABLE 5

| Test concentration | | Percentage induction of caspase-3 enzyme activation with respect to untreated |
|---|---|---|
| Untreated | | 0.00 |
| Anthralin-0.1 µM | | 101.85 |
| IS 181 | 100 | −20.37 |
| (µg/ml) | 500 | 7.41 |
| | 1000 | 29.63 |
| | 2000 | 50.00 |
| | 5000 | Couldn't be tested due very low amount of protein due to necrotic cell death |

Example 9: DNA Fragmentation Assay

Figures 8A, 8B:
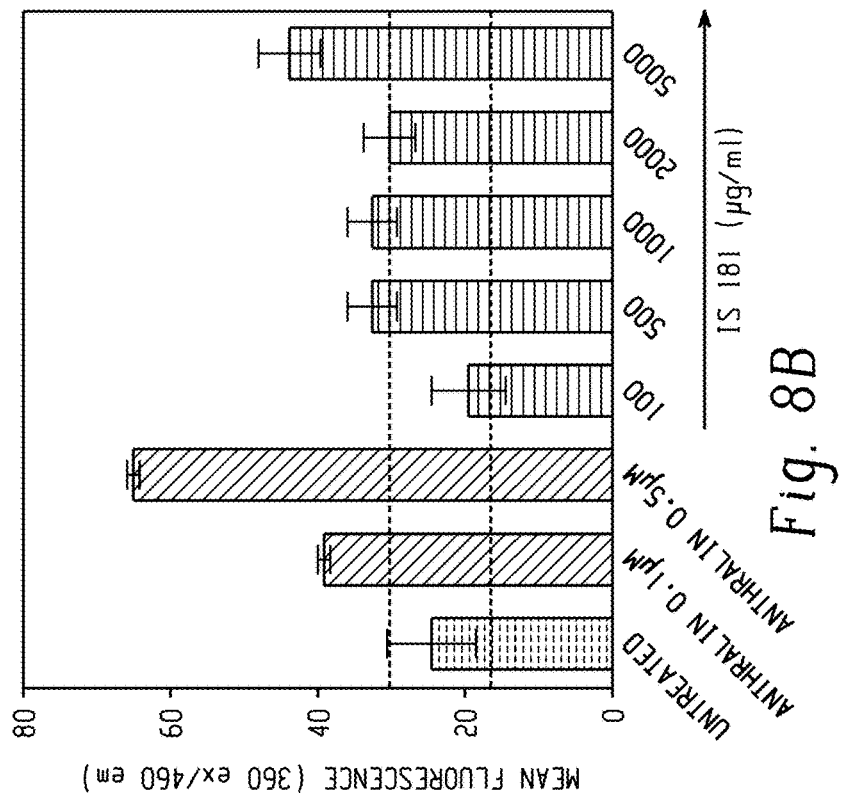
FIGS. 8A-8B: Shows DNA Fragmentation results.

Cell lines: Human Keratinocytes (HaCaT); Test Item (TI): IS 181; Treatment regimen; Multiple additions (2)—48 h; Concentration range: 100 µg/ml to 5000 µg/ml (Duplicate wells); Sera Condition: Medium containing 1% FBS: Method of estimation: HaCaT cells were plated in medium containing 10% FBS; The cells were then subjected to serum starvation in 1% FBS. Cells were treated with IS 181 for 48 h (retreatment was given after 24 h, hence two additions). Cells were lysed and fragmented DNA was precipitated using PEG/NaCl solution. The fragmented DNA was incubated with 0.2 µg/ml of Hoechst 33258 dye and fluorescence was read at 360 ex/460 em. End point: Percentage induction of DNA fragmentation with respect to untreated Positive control. Anthralin. IS 181 led to induction of DNA fragmentation in HaCaT cells at all the concentrations tested except at 100 µg/ml. A maximum of 83.3% percent induction of DNA fragmentation with respect to untreated was observed at 5000 µg/ml of IS 181 after 48 h of treatment. The overall effect of IS 181 on induction of DNA fragmentation with respect to untreated in HaCaT cells ranged from −18.8% to 83.3%. (FIG. 8 and Table-6).

TABLE 6

| | Test Concentration | % induction of DNA fragmentation |
|---|---|---|
| | Untreated | 0.00 |
| IS 181 | 100 | −18.8 |
| µg/m | 500 | 35.4 |
| | 1000 | 35.4 |
| | 2000 | 27.1 |
| | 5000 | 83.3 |
| Anthralin | 0.1 | 60.42 |
| (µM) | 0.5 | 168.75 |

Example 10: LDH Assay: Effect on LDH Enzyme Release in Culture Supernatant

Cell line: HaCaT (Human keratinocyte); Test item: IS 181; Treatment regimen: Single addition—24 hours; Concentration range: 400 µg/ml-2000 µg/ml; Sera Condition: Medium containing 1% FBS; Method: Evaluation of LDH levels in supernatants of treated cells with respect to untreated. End-point: Percentage increase in LDH activity in treated cells with respect to untreated.

LDH Assay Results-24 Hours Data:

HaCaT cells were treated with IS 181 at concentrations around IC50 value. The supernatants were collected after 24 hours. IS181 led to significant increase in LDH enzyme release (>50% with respect to untreated) at 24 h which is indicative of secondary necrosis. The above observation coincides with the occurrence of mitochondrial membrane depolarization as observed at 20 h at similar doses of IS181.

TABLE 7

LDH enzyme activity

| Concentration (µg/ml) | LDH Activity (mU/ml) | % Increase with respect to untreated |
|---|---|---|
| Untreated | 63.26 | |
| 400 | 79.73 | 26.03 |
| 475 | 94.71 | ***49.73 |
| 500 | 85.25 | **34.76 |
| 750 | 120.47 | ***90.43 |
| 1000 | 136.82 | ***116.28 |
| 2000 | 138.60 | ***119.09 |

Each value represents the mean of triplicate wells;
Statistical comparison with untreated was conducted using two - way analysis of variance (ANOVA) with Bonferroni post-tests (Graphpad prism software version 4), [2];
***represents significant difference with $p < 0.001$;
**represents significant difference with $p < 0.01$ Positive control: Doxorubicin and Triton X

TABLE 8

Effect of positive controls

| Test Concentration | LDH Activity (mU/ml) | % Increase with respect to untreated |
|---|---|---|
| Doxorubicin | | |
| Untreated | 63.26 | |
| 0.1 μM | 60.23 | −4.78 |
| 1 μM | 52.87 | −16.43 |
| 10 μM | 142.92 | ***125.92 |
| Triton X-100 | | |
| Untreated | 63.26 | |
| #0.01% | 44.11 | −30.27 |
| #0.1% | 123.88 | ***95.84 |

Each value represents the mean of triplicate wells;
Statistical comparison with untreated was conducted using two - way analysis of variance (ANOVA) with Bonferroni post-tests (Graphpad prism software version 4), [6];
***represents significant difference with $p < 0.001$

Example 11: Inhibition of Endothelial Cell Proliferation

Figure 9B:
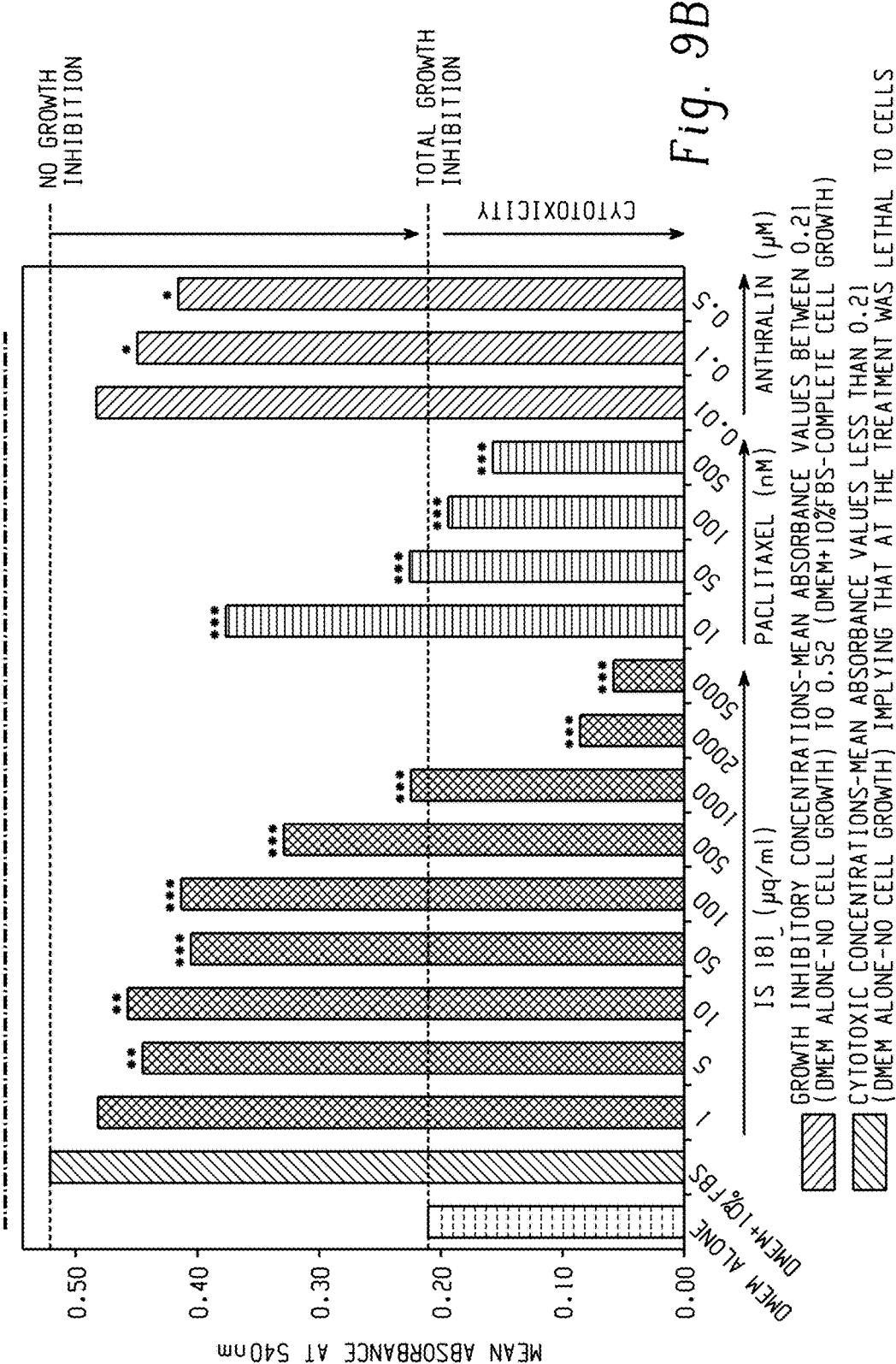

Cell line: Human endothelial cells (EA.hy 926); test item: IS 181: treatment regimen: multiple additions (3)-72 hours; concentration range: 1 6 g/ml to 5000 6 g/ml (triplicate wells); sera condition: medium containing 10% FBS. EA.hy926 cells were plated in medium containing 10% FBS. The cells were then subjected to complete serum starvation. The cells were retreated with 10% FBS to stimulate cellular proliferation. Cells were treated with IS 181 for 72 hours (retreatment was given after 24 hence three additions). Inhibition of FBS stimulated cell proliferation was measured using MTT assay. End point: percentage inhibition of FBS stimulated cell proliferation. Positive controls: anthralin; paclitaxel. IS 181 led to significant inhibition of FBS stimulated cell proliferation at concentrations ranging from 5 μg/ml to 1000 μg/ml. At higher concentrations of 2000 μg/ml to 5000 μg/ml, IS 181 was found to exhibit cytotoxic effects (FIGS. 9A-9B and Table-9).

TABLE 9

| Test concentration | | Absorbance (Mean ± SD) at 540 nm | ¾ Inhibition of FBS stimulated cell growth |
|---|---|---|---|
| DMEM alone | | 0.21 ± 0.0004 | 60.31 |
| DMEM + 10% FBS | | 0.52 ± 0.015 | 0.00 |
| IS 181 (μg/ml) | 1 | 0.48 ± 0.006 | 7.47 |
| | 5 | 0.45 ± 0.027 | 14.36 |
| | 10 | 0.46 ± 0.012 | 12.38 |
| | 50 | 0.41 ± 0.011 | 21.69 |
| | 100 | 0.41 ± 0.012 | 21.00 |
| | 500 | 0.33 ± 0.004 | 36.76 |
| | 1000 | 0.22 ± 0.008 | 56.99 |
| | 2000 | 0.09 ± 0.0003 | 83.66 |
| Paclitaxel (nM) | 10 | 0.36 ± 0.012 | 27.57 |
| | 50 | 0.23 ± 0.008 | 58.92 |
| | 100 | 0.19 ± 0.006 | 62.73 |
| | 500 | 0.16 ± 0.003 | 70.07 |
| | 1000 | 0.06 ± 0.001 | 89.41 |
| Anthralin (μM) | 0.01 | 0.46 ± 0.025 | 7.21 |
| | 0.1 | 0.45 ± 0.018 | 14.61 |
| | 0.5 | 0.42 ± 0.013 | 20.36 |

Example 12: DNA Fragmentation in Endothelial Cells

Figures 10A, 10B:
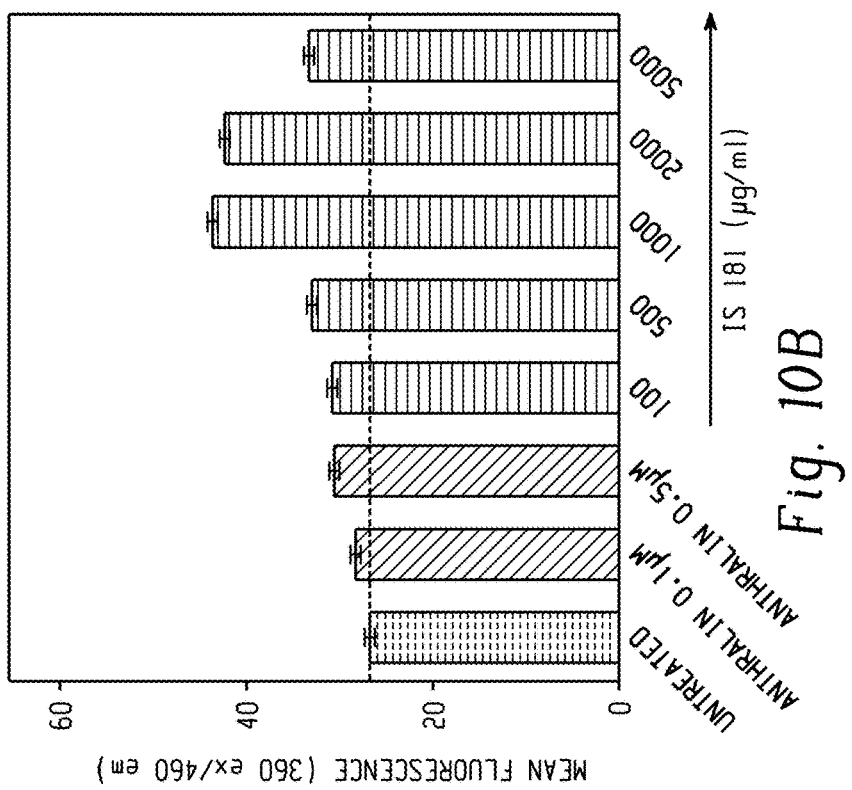
FIGS. 10A-10B: Effect of IS 181 on DNA fragmentation in endothelial cells.
Figure 11A:
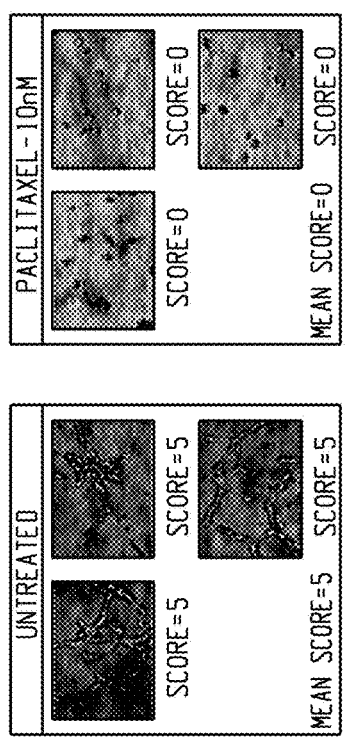
FIGS. 11A-11G: Photomicrographs showing tube formation in endothelial cells.
Figure 11B:
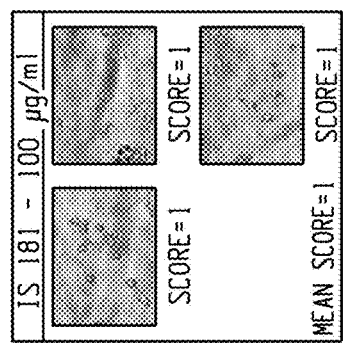
Figure 11C:
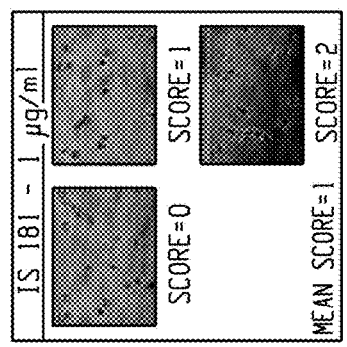
Figure 11D:
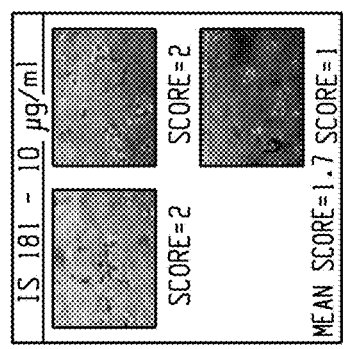
Figure 11E:
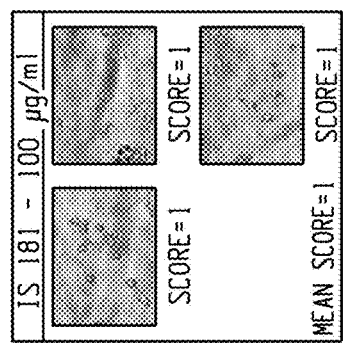
Figure 11F:
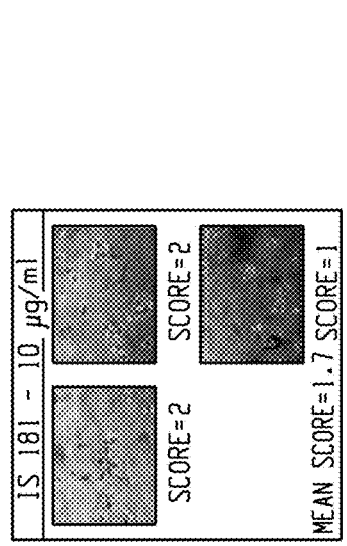
Figure 11G:
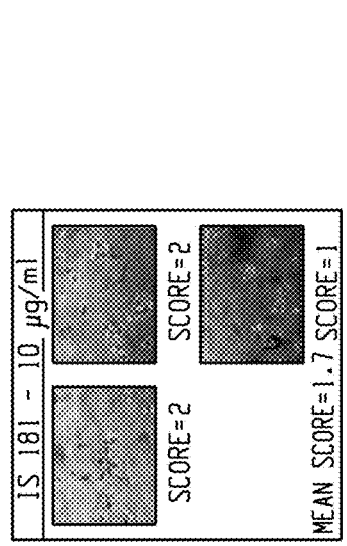

Cell lines: Human endothelial cells (EA.Hy 926); test item: IS 181; treatment regimen: multiple additions (2)—48 hours; concentration range: 100 μg/ml to 5000 μg/ml (Duplicate wells); sera condition: medium containing 1% FBS. EA.hy926 cells were plated in medium containing 10% FBS. The cells were then subjected to serum starvation in 1% FBS. Cells were treated with IS 181 for 48 h (retreatment was given after 24 h, hence two additions). Cells were lysed and fragmented DNA was precipitated using PEG/NaCl solution. The fragmented DNA was incubated with 0.2 μg/ml of Hoechst 33258 dye and fluorescence was read at 360 ex/460 em. End point: Percentage induction of DNA fragmentation with respect to untreated. Positive control: anthralin. IS 181 led to induction of DNA fragmentation in Ea.hy.926 cells at all the concentrations tested. A maximum of 64.15% percent induction of DNA fragmentation with respect to untreated was observed at 1000 μg/ml of IS 181 after 48 h of treatment. The overall effect of IS 181 on induction of DNA fragmentation with respect to untreated in Ea.hy.926 cells ranged from 15.09% to 64.15% (FIGS. 10A-10B and Table-10).

TABLE 10

| Test Concentration | | % induction of DNA fragmentation |
|---|---|---|
| | Untreated | 0.00 |
| IS 181 μg/ml | 100 | 15.09 |
| | 500 | 22.64 |
| | 1000 | 64.15 |
| | 2000 | 56.60 |
| | 5000 | 22.64 |
| Anthralin (μM) | 0.1 | 3.77 |
| | 0.5 | 13.21 |

Example 13: Tube Formation in Endothelial Cells

Cell lines: Human endothelial cells (EA.Hy 926); test item: IS 181; treatment regimen; multiple additions (2)—48 hours; concentration range: 100 6 g/ml to 5000 6 g/ml (Duplicate wells); sera condition: medium containing 1% FBS. Non-cytotoxic concentrations of IS 181 were determined using MTT assay. EA.hy926 cells were plated on ECMatrix solution. Cells were treated with IS 181 for 8 hours. Endothelial tubes were visualized under inverted light microscope at 40× magnification and images were captured. End point: visual pattern recognition and scoring of photomicrographs (FIGS. 11A-11G) based on Table-11 below:

TABLE 11

| Pattern | Value |
|---|---|
| Individual cells well separated | 0 |
| Cells begin to migrate and align them selves | 1 |
| Capillary tube visible. No sprouting | 2 |
| Sprouting of new capillary tubes visible | 3 |
| Closed polygons begin to form | 4 |
| Complex mesh like structures develop | 5 |

Positive control: Paclitaxel. IS 181 was observed to block endothelial tube formation by Ea.hy.926 cells at all the test concentrations ranging from 1 6 g/ml to 1000 6 g/m/1.

Figure 12:
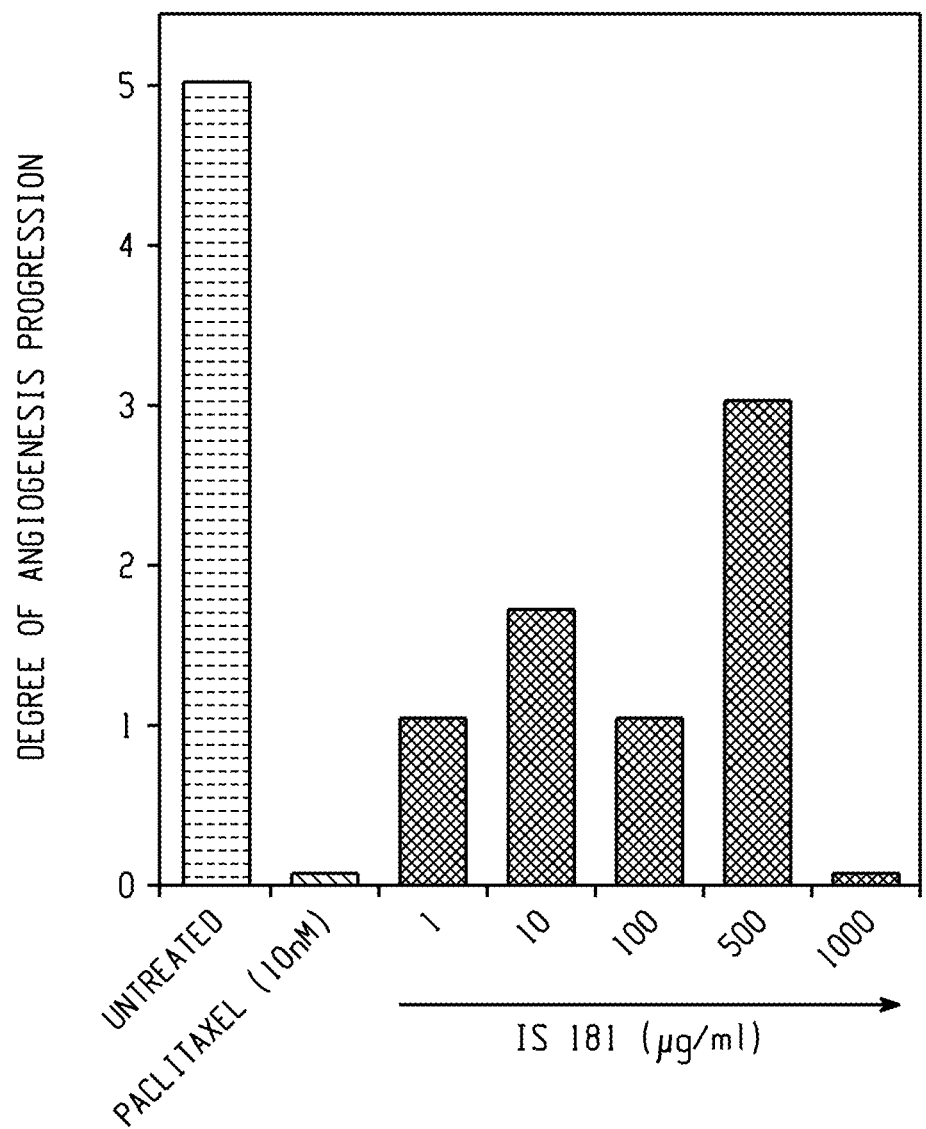
FIG. 12: Angiogenesis progression in Ea.hy.926 cells after 8 hours of treatment with IS 181.

Complete inhibition of endothelial morphogenesis on matrigel was obtained at 1000 6 g/ml of IS 181 (FIG. 12).

Example 14: Inhibition of Endothelial Cell Migration

Figure 13:
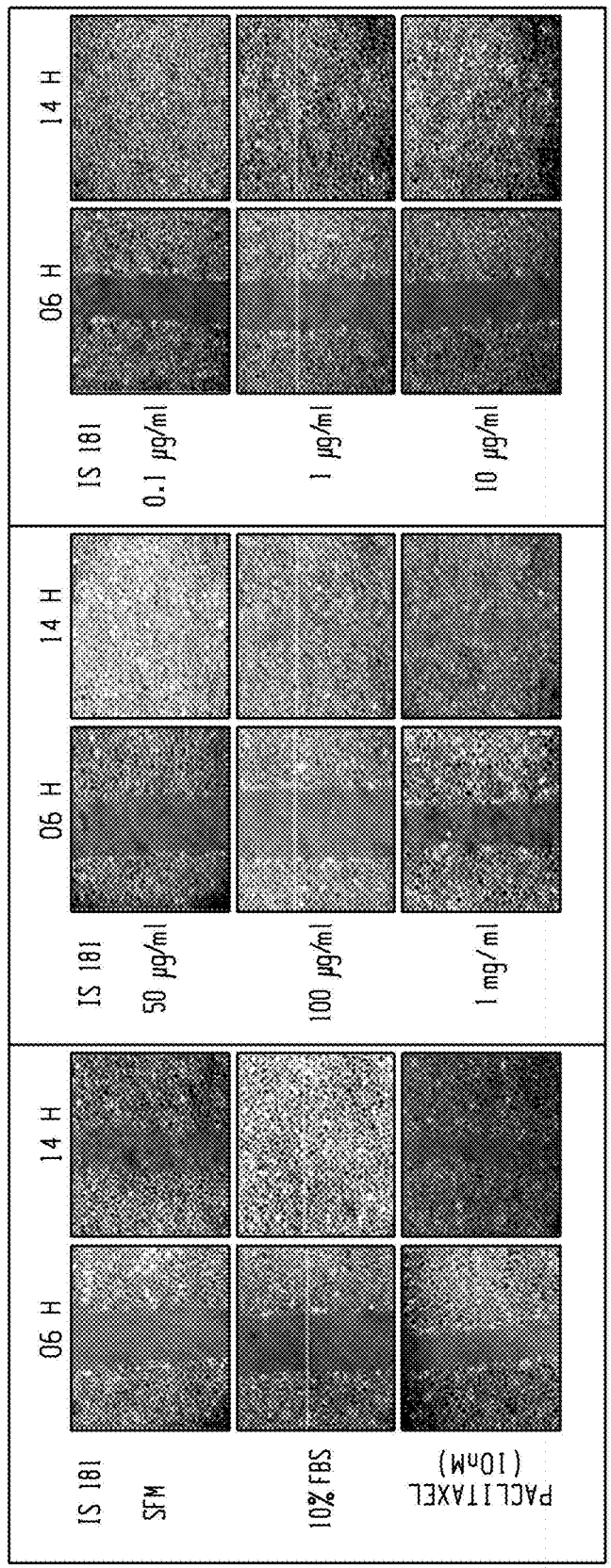
FIG. 13: Photomicrographs showing inhibition of endothelial cell migration.
Figures 14A, 14B:
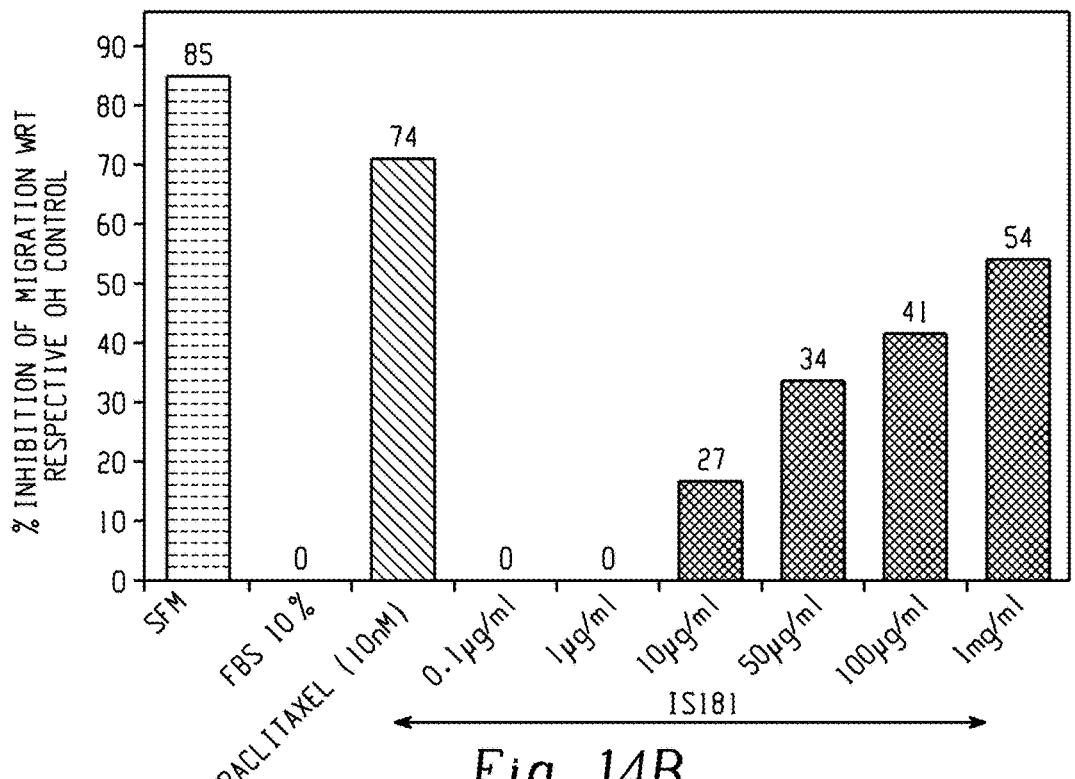
FIGS. 14A-14B: Effect of IS 181 on inhibition of human endothelial (EA.hy926) cells.

Cell line: Human endothelial cells (EA.hy 926); test item: IS 181; treatment regimen: single addition; concentration range: 0.1 µg/ml-1 mg/ml; sera condition: medium containing 10% FBS. EA.hy926 cells were plated in medium containing 10% FBS. The cells were then subjected to serum starved with medium containing 1% FBS for 24 hours. 24 hours post serum starvation, the wounds (straight line) were created in the middle of the well using a sterile 200 µl pipette tip. Cells were washed twice using DMEM followed by treatment with different concentrations of IS 181 in DMEM containing 10% FBS. Images of wound were taken at 0 h and 14 h at three points in single well and distance of wound closure was measured using Image J software. End point: image analysis of cell migration of different concentrations of IS 181 treated cells at 0 hour and after 14 hours of treatment. Percentage inhibition in cell migration of different concentrations of IS 181 treated cells were calculated after 14 h of treatment with respect to respective 0 hours (FIG. 13). IS 181 demonstrated 17%-54% inhibition of migration of EA.hy926 cells at concentrations ranging from 10 µg/ml-1 mg/ml. (FIGS. 14A-14B).

TABLE 12

| Concentrations | | % Inhibition of migration with respect to respective 0 h control |
|---|---|---|
| SFM | | 85 |
| FBS 10% | | 0 |
| Paclitaxel (10 nM) | | 71 |
| IS 181 | 0.1 µg/ml | 0 |
| | 1 µg/ml | 0 |
| | 10 µg/ml | 17 |
| | 50 µg/ml | 34 |
| | 100 µg/ml | 41 |
| | 1 mg/ml | 54 |

Example 15: VEGF Inhibition in Keratinocytes

Figures 15A, 15B:
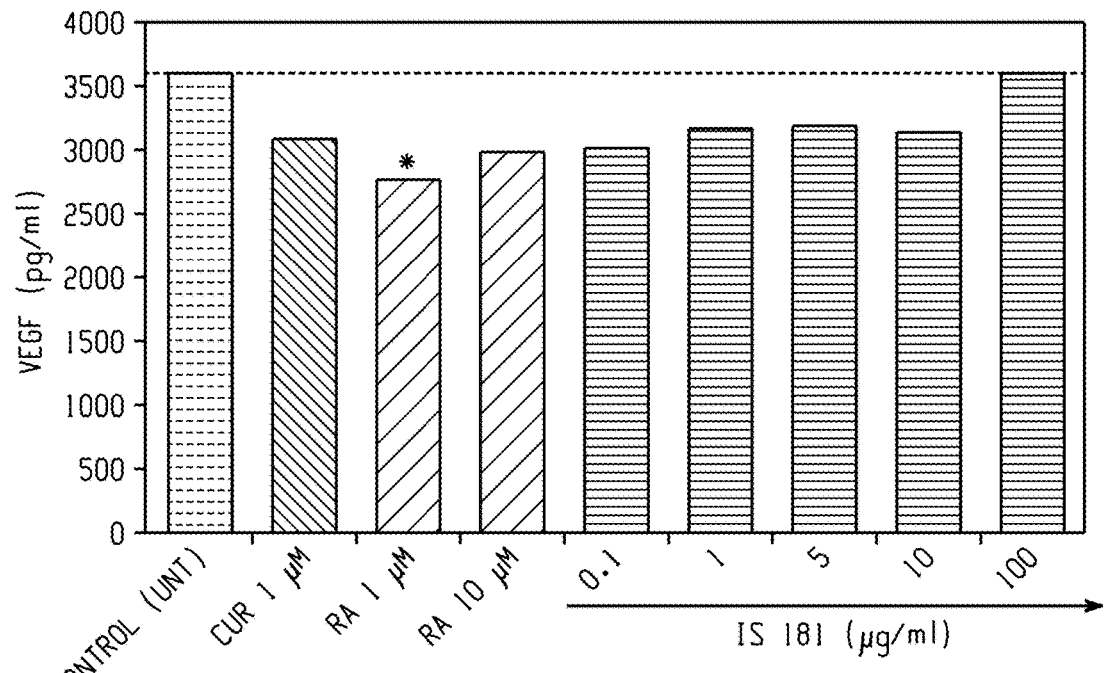
FIGS. 15A-15B: Inhibitory effect of IS 181 on VEGF secretion in HaCaT cells after 24 hours.

Cell lines: Human Keratinocytes (HaCaT); test item: IS181; treatment regimen: single addition—24 hours; concentration range: 0.1 µg/ml-100 µg/ml. HaCaT cells were plated in medium containing 10% FBS for 24 hours. Cells were serum-starved for another 24 hours (0% FBS). Cells were treated with IS181 for 24 hours. Supernatants were collected and stored at −20° C. till analysed. Levels of VEGF were analysed in supernatants by ELISA. Percent inhibition of VEGF secretion was calculated with reference to untreated levels. Positive control: curcumin; retinoic acid (at non-cytotoxic concentrations). IS 181 (0.1 6 g/ml-10 6 g/ml) demonstrated 11.1%-17% inhibition of VEGF secretion as compared to untreated (basal) levels. Treatment of HaCaT cells with RA at 1 6M resulted in 22.8% VEGF inhibition as compared to untreated (basal) levels. Curcumin at 20 uM and RA at 50 uM did not result in any VEGF inhibition (FIGS. 15A-15B) and Table-13.

TABLE 13

| SAMPLES | | Conc. of VEGF (pg/ml) | % Inhibition of VEGF wrt untreated (basal) levels |
|---|---|---|---|
| Contral (Untretaed) | | 3592.7 | 0 |
| Cur 1 µM | | 3059.1 | 14.9 |
| RA 1 µM | | 2775.1* | 22.8 |
| RA 10 µM | | 2982.4 | 17.0 |
| IS181 (µg/ml) | 0.1 | 2982.4 | 17.0 |
| | 1 | 3139.7 | 12.6 |
| | 5 | 3193.5 | 11.1 |
| | 10 | 3128.2 | 12.9 |
| | 100 | 3565.8 | 0.7 |

Example 16: Evaluation of Anti-Inflammatory Activity of IS181 in RAW264.7 Cells

Figure 16:
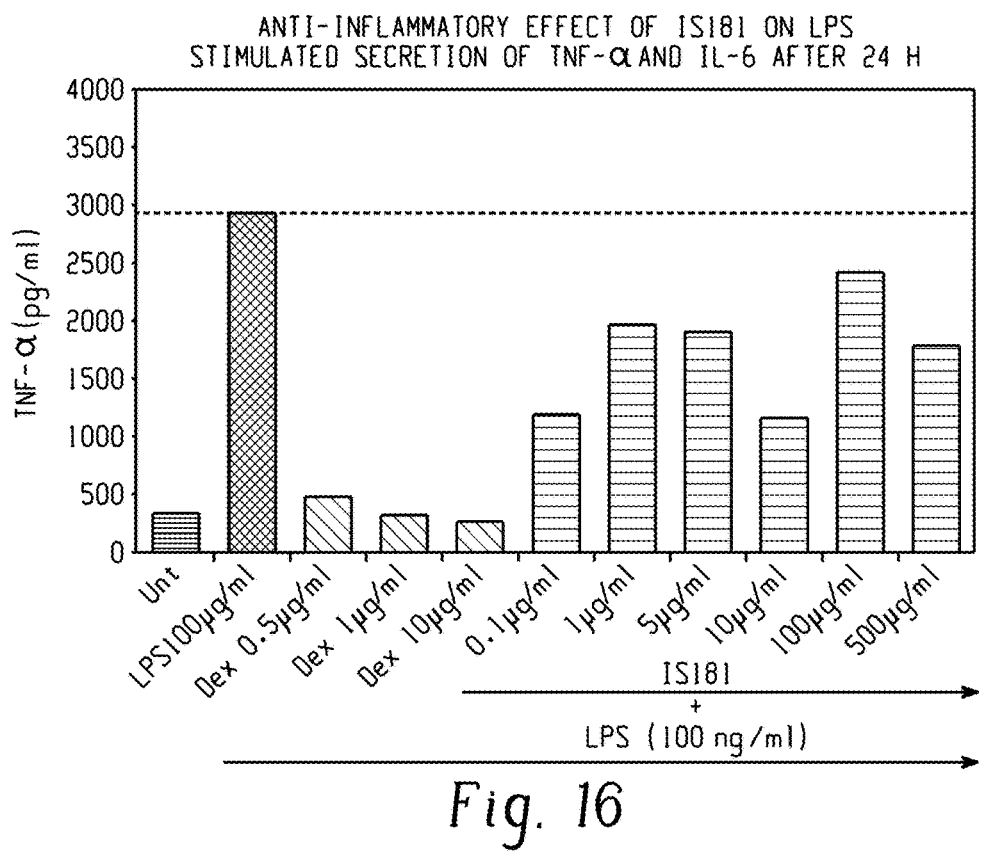
FIG. 16: Anti-inflammatory effect of IS 181 on LPS stimulated secretion of TNF-α.
Figure 17:
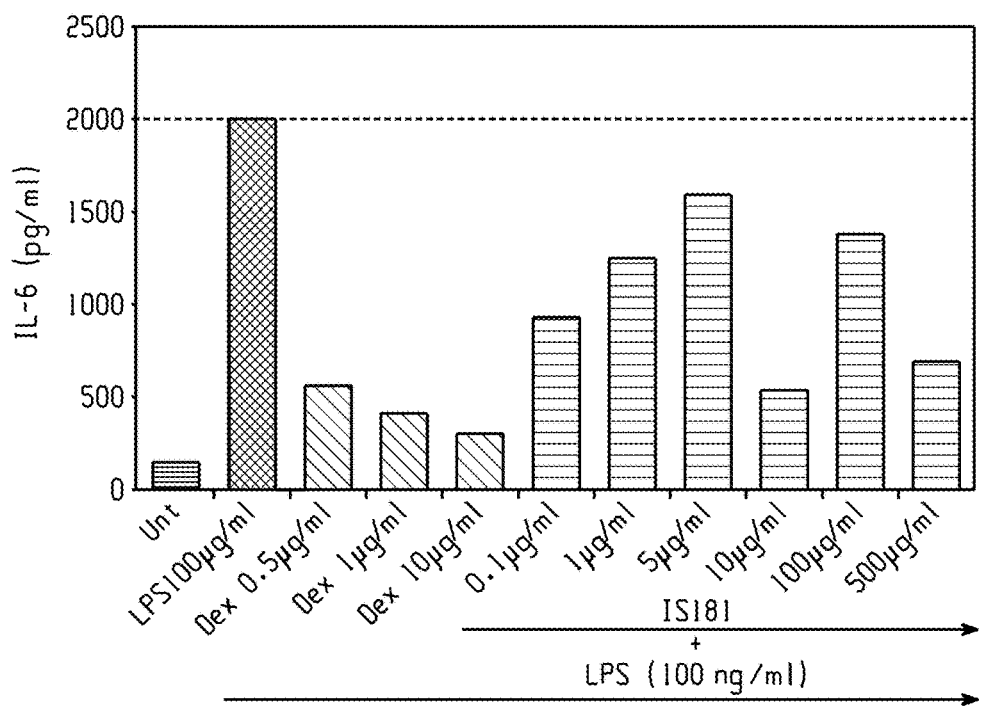
FIG. 17: Anti-inflammatory effect of IS 181 on LPS stimulated secretion of IL-6.
Figure 18:
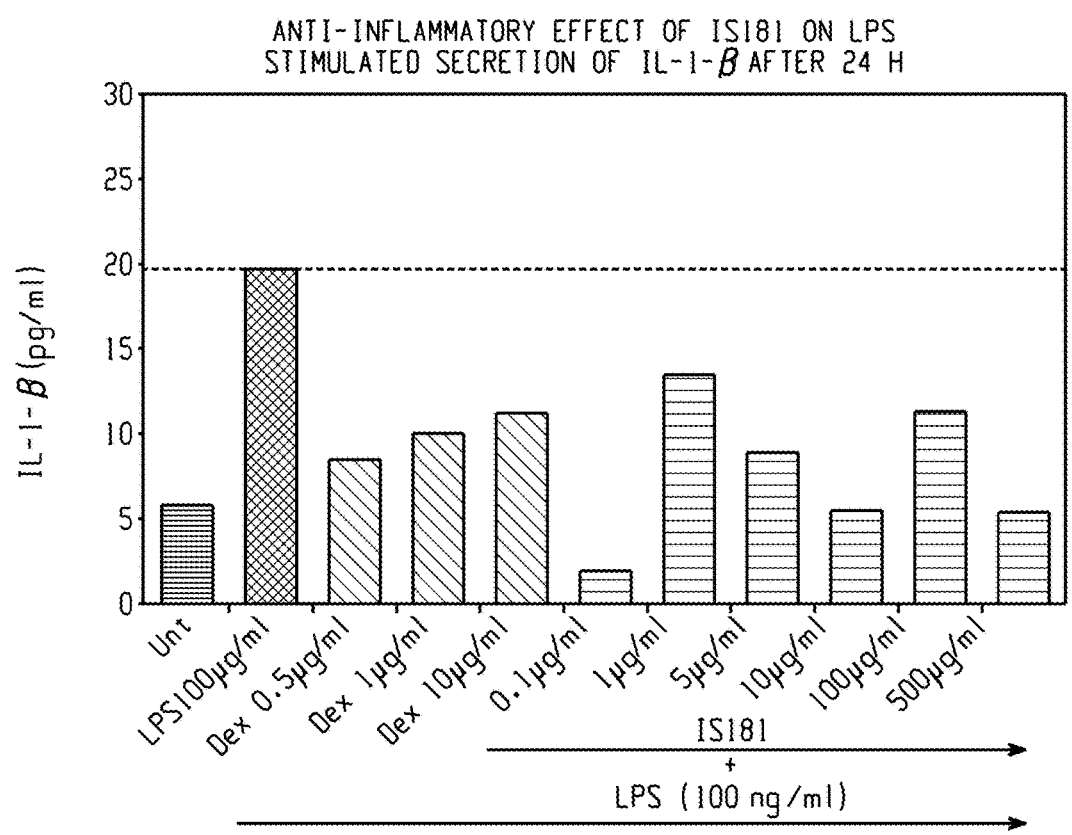
FIG. 18: Anti-inflammatory effect of IS 181 on LPS stimulated secretion of IL-1-β after 24 hours.

Effect on pro-inflammatory cytokines against LPS stimulation: TNF-α; IL-6; IL-1-β: Cell lines: Murine macrophage cell line (RAW264.7); test item: IS181; experimental steps: pretreatment of cells with TI for 2 hours; stimulation with LPS (100 ng/ml) for 24 hours; supernatant collection for cytokine analysis; concentration range: o.1 µg/ml-500 µg/ml (duplicate wells); Cytokines: TNF-α; IL-6; IL-1-β; Method of estimating cytokines: ELISA; positive control: dexamethasone. IS181 demonstrated good extent of TNF-α and IL-6 inhibition as compared to LPS stimulated levels (Figures-16 and 17). IS181 demonstrated good extent of IL-1-β inhibition as compared to LPS stimulated levels (FIG. 18).

Example 17: Evaluation of Anti-Inflammatory Activity of IS181 in HaCaT Cells

Figure 19:
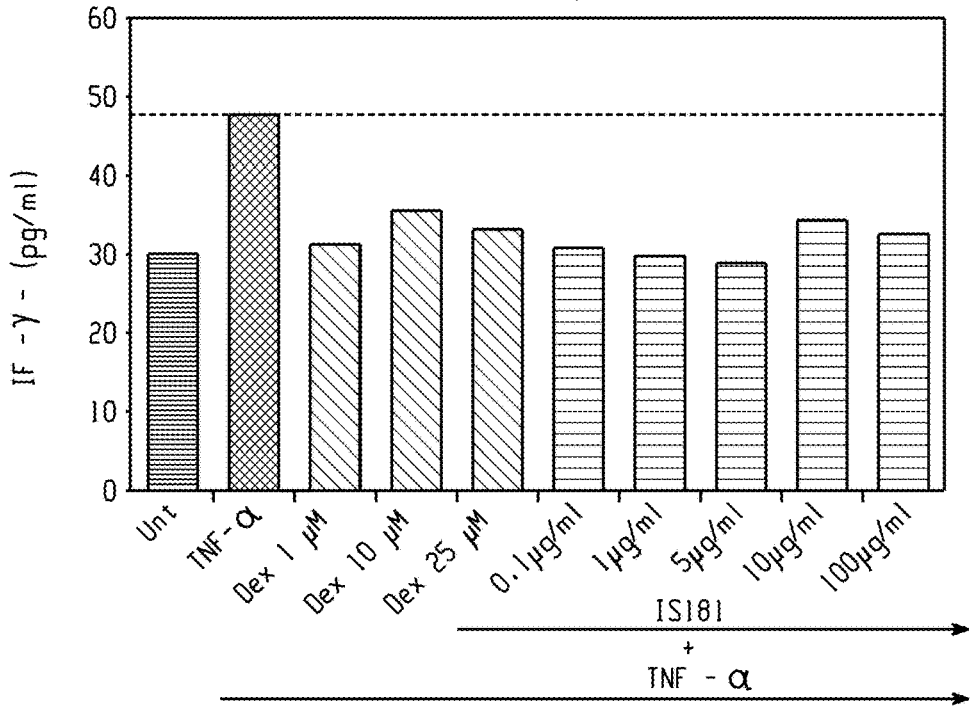
FIG. 19: Anti-inflammatory effect of IS 181 on TNF-α stimulated secretion of IFN-γ after 24 hours.
Figure 20:
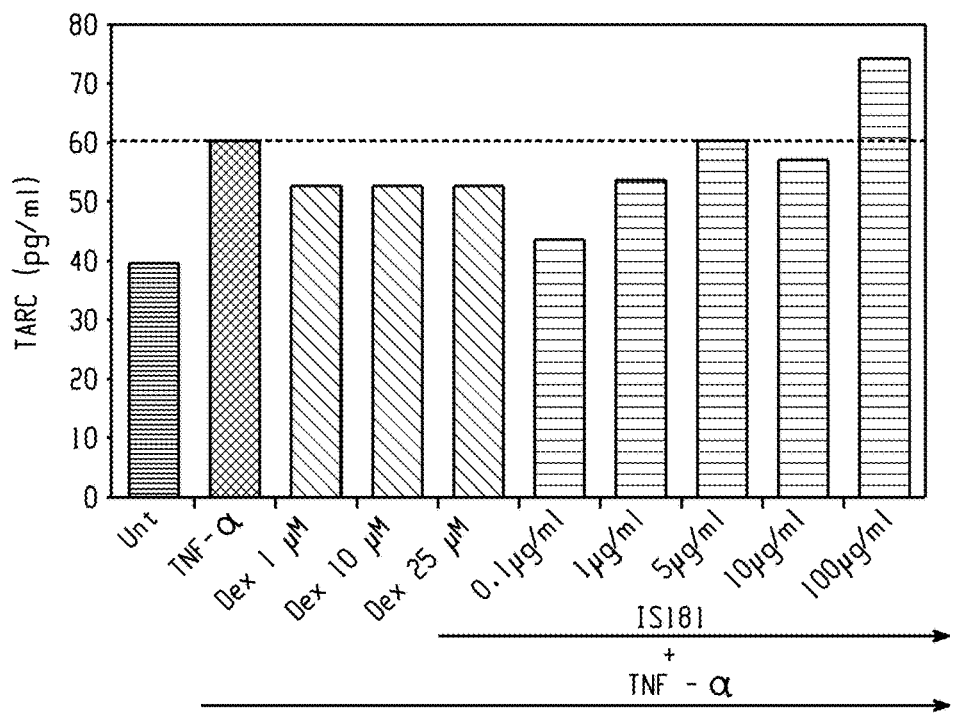
FIG. 20: Anti-inflammatory effect of IS 181 on TNF-α stimulated secretion of TARC after 24 hours.
Figure 21:
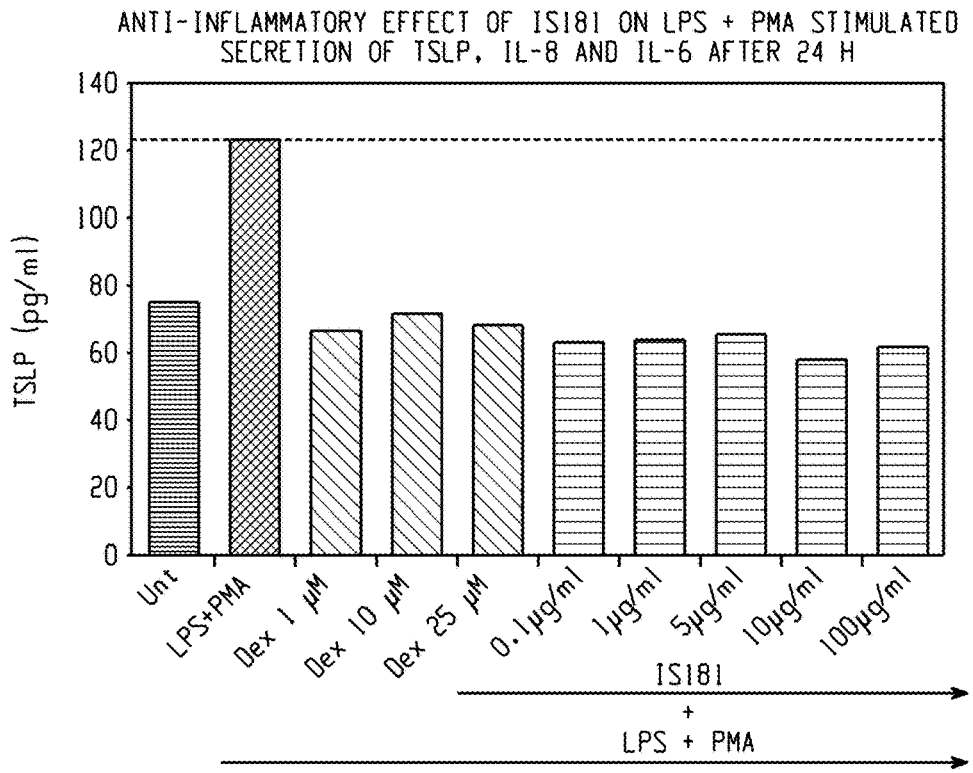
FIG. 21: Anti-inflammatory effect of IS 181 on LPS+PMA stimulated secretion of TSLP after 24 hours.
Figure 22:
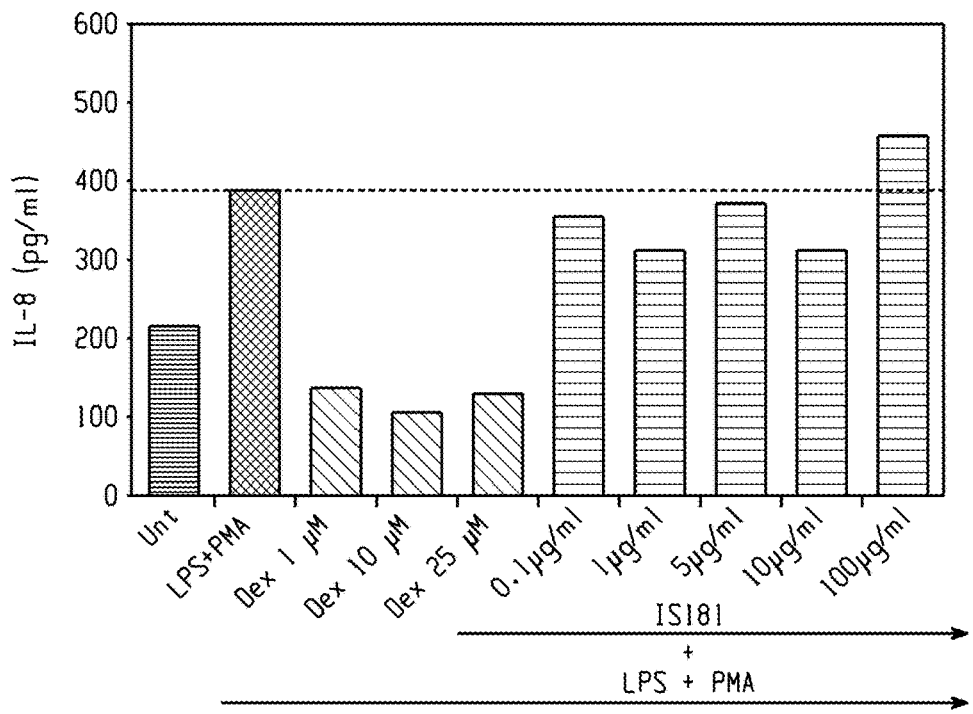
FIG. 22: Anti-inflammatory effect of IS 181 on LPS+PMA stimulated secretion of IL-8 after 24 hours.

Effect on pro-inflammatory cytokines against TNF-α/LPS+PMA stimulation: TNF-α; IFN-γ; TARC; TSLP; IL-6; IL-8: Cell lines: Human keratinocytes (HaCaT); test item (TI); IS181; experimental steps: pre-treatment of cells with TI for 2 hours; stimulation with TNF-α: 20 ng/ml; stimulation with LPS+PMA-10 µg/ml LPS+40 ng/ml PMA; supernatant collection for cytokine analysis after 24 hours; concentration range: 0.1 µg/ml-100 µg/ml (duplicate wells); cytokines: TNF-α; IFN-γ; TARC; TSLP; IL-6; IL-8. Method of estimating cytokines: ELISA; positive control: dexamethasone. IS181 demonstrated good extent of IFN-γ and TARC inhibition as compared to LPS stimulated levels (Figures-19 and 20). IS181 demonstrated good extent of TSLP and IL-8 inhibition as compared to LPS stimulated levels (Figures-21 and 22).

Figure 23:
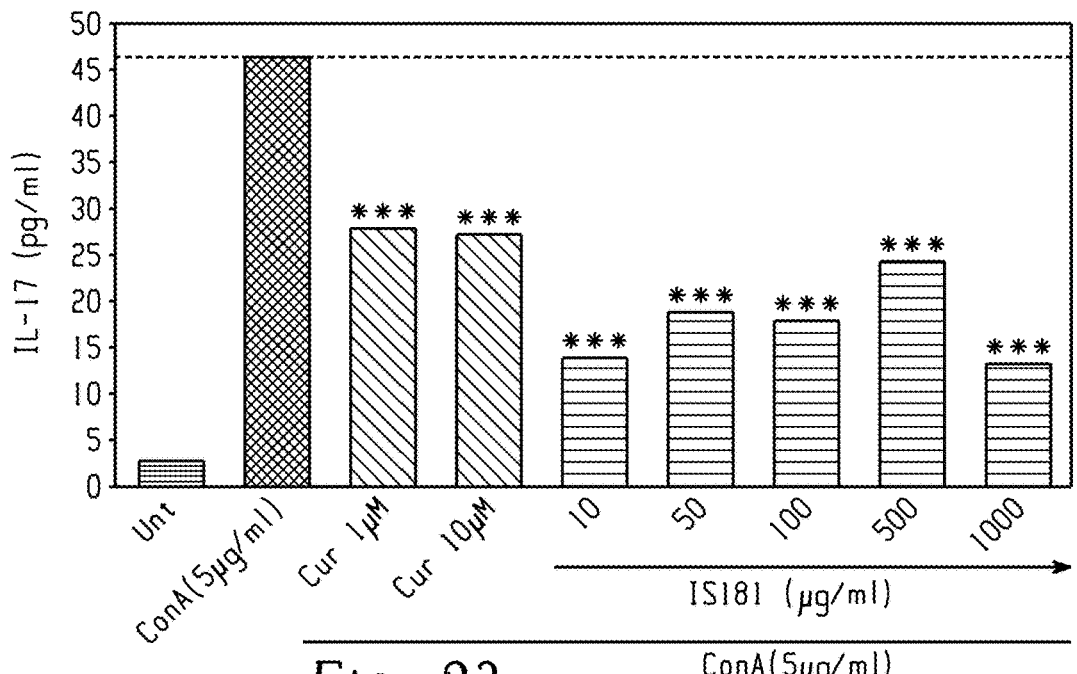
FIG. 23: Inhibitory effect of IS 181 on IL-17 secretion in splenocytes after 24 hours.

Example 18: Evaluation of Anti-Inflammatory Activity of IS181 by IL-17 Inhibition in Splenocytes Cell lines: mouse splenocytes; test item: IS181; treatment regimen: single addition—24 hours; concentration range: 10 µg/ml-5000 µg/ml.A) Identification of non-cytotoxic concentrations: splenocytes were treated with IS181 for 24 hours. Effect on cell viability was assessed by MTT assay. Concentrations leading to >75% cell viability were selected for IL-17 assay. B) IL-17 assay: splenocytes were treated with IS181 in presence of ConA stimulation for 24 hours. Supernatants were collected and stored at −20° C. till analysed. Levels of IL-17 were analysed in supernatants by ELISA. Percent inhibition of IL-17 secretion was calculated with reference to ConA treated levels. Positive control: curcumin. IS 181 resulted in >75% cell viability or <25% cytotoxicity in the concentration range of 10 6 g/ml-1 mg/ml. At 2 mg/ml and 5 mg/ml, IS 181 resulted in 48.4% and 74.4% cytotoxicity respectively. Hence, non-cytotoxic/safe concentrations for IS 181 were taken as 10 6 g/ml-1 mg/ml for IL-17 assay (Table 14). Curcumin (1 6M and 10 6M) demonstrated >75% cell viability. Hence these concentrations were selected as safe for conducting IL-17 assay. IS 181 (10 6 g/ml-1 mg/ml) demonstrated 48.2%-71.4% inhibition of IL-17 secretion as compared to Control (ConA) levels. Curcumin at 1 6M and 10 6M resulted in inhibition of IL-17 by 40.5% and 42.5% respectively (FIG. 23 and Table-15).

TABLE 14

| Sample | Conc | Cell viability |
|---|---|---|
| Curcumin | 1 μM | 97.5 |
|  | 10 μM | 82.0 |
|  | 20 μM | 40.4 |
| IS 181 | 10 μg/ml | 97.0 |
|  | 50 μg/ml | 109.7 |
|  | 100 μg/ml | 110.0 |
|  | 500 μg/ml | 94.6 |
|  | 1 mg/ml | 79.4 |
|  | 2 mg/ml | 51.6 |
|  | 5 mg/ml | 25.6 |

TABLE 15

| SAMPLES | | Conc. of IL-17 (pg/ml) | % Inhibition of IL-17 wrt Control (ConA) |
|---|---|---|---|
| Control (ConA) | | 46.5 | 0 |
| Cur 1 μM | | 27.7 | 40.5 |
| Cur 10 μM | | 26.7 | 42.5 |
| IS181 (μg/ml) + ConA | 10 | 13.3 | 71.4 |
|  | 50 | 18.8 | 59.5 |
|  | 100 | 17.6 | 62.1 |
|  | 500 | 24.1 | 48.2 |
|  | 1000 | 19.2 | 58.8 |

Example 19: Evaluation of Anti-Inflammatory Activity of IS-181 by IL-23 Inhibition in Immune Cells (Human Monocytes THP-1)

Figure 24:
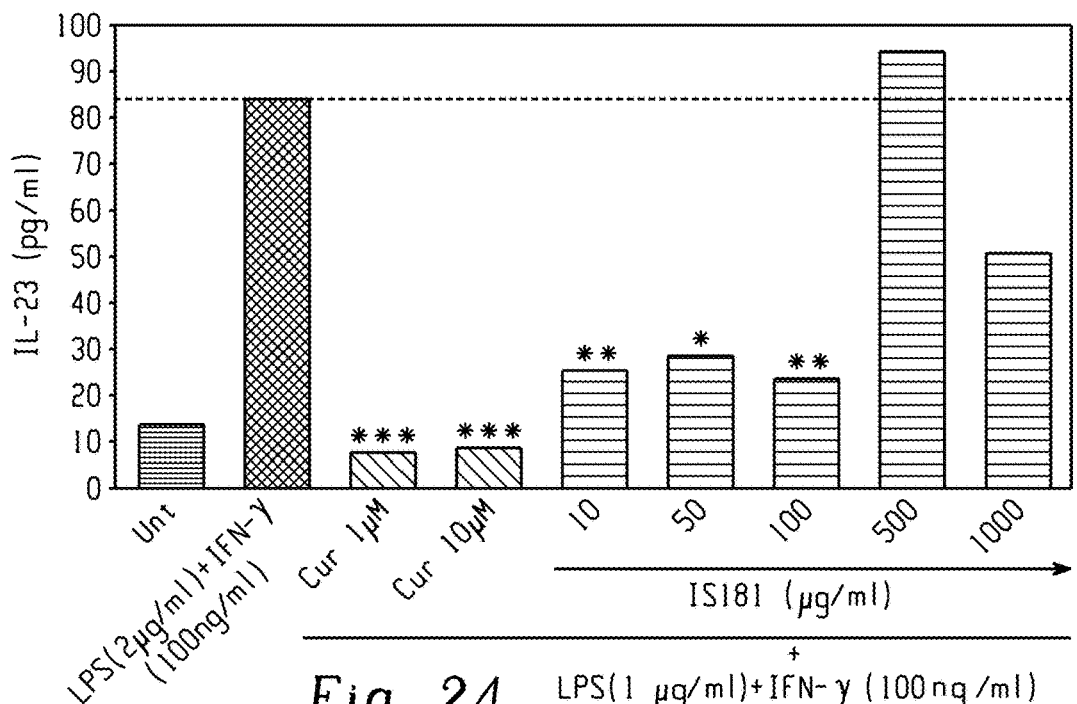
FIG. 24: Inhibitory effect of IS 181 on IL-23 secretion by THP-1 after 24 hours.

Cell lines: Human monocytic cell line (THP-1); test item: IS181: treatment regimen; single addition—24 hours; concentration range: 10 μg/ml-5000 μg/ml. A) Identification of non-cytotoxic concentrations: THP-1 cells were treated with IS181 for 24 hours; effect on cell viability was assessed by MTT assay; concentrations leading to >75% cell viability were selected for IL-23 assay. B) IL-23 assay: THP-1 cells were treated with IS181 in presence of LPS (1 μm/ml)+IFN-γ (100 ng/ml) stimulation for 24 hours; supernatants were collected and stored at −20° C. till analysed; levels of IL-23 were analysed in supernatants by ELISA; percent inhibition of IL-23 secretion was calculated with reference to LPS (1 μg/ml)+IFN-γ (100 ng/ml) treated levels. Positive control: curcumin. IS 181 resulted in >75% cell viability or 25% cytotoxicity in the concentration range of 10 μg/ml-500 μg/ml. At 1 mg/ml and 5 mg/ml, IS 181 resulted in 38.7% and 85% cytotoxicity respectively. Hence following non-cytotoxic/safe concentrations for IS 181 were selected for IL-23 assay: 10 μg/ml, 50 μg/ml, 100 μg/ml, 500 μg/ml. Since supernatants corresponding to 5 concentrations were to be tested for IL-17 activity, we also tested 1 mg/ml. Curcumin (positive control) resulted in >75% cell viability or 25% cytotoxicity at 1 μM, 10 μM and 20 μM (Table 16). Hence IL-23 secretion was estimated at 10 μM and 20 μM. IS 181 demonstrated 69.8%, 66.3% and 72.3% inhibition of IL-23 secretion at 10 6 g/ml, 50 6 g/ml, and 100 6 g/ml as compared to control (LPS 1 6 g/ml+IFN-γ 100 ng/ml) levels. Treatment of HaCaT cells with Curcumin at 1 6M and 10 6M resulted in 91.6% and 90.6% inhibition of IL-23 with respect to Control (LPS 1 6 g/ml+IFN-γ 100 ng/ml) levels respectively (Table-17 and FIG. 24).

TABLE 16

| Sample | Conc | Cell viability (wrt Untreated) |
|---|---|---|
| Curcumin | 1 μM | 94.7 |
|  | 10 μM | 103.3 |
|  | 20 μM | 107.0 |
| IS 181 | 10 μg/ml | 81.2 |
|  | 50 μg/ml | 84.2 |
|  | 100 μg/ml | 90.4 |
|  | 500 μg/ml | 88.5 |
|  | 1 mg/ml | 61.3 |
|  | 5 mg/ml | 15.0 |

TABLE 17

| SAMPLES | | Conc. of IL-23 (pg/ml) | % Inhibition of IL-23 wrt Control (LPS + IFN-γ) |
|---|---|---|---|
| Control [LPS (1 μg/ml) + IFN-γ (100 ng/ml)] | | 64.2 | 0 |
| Cur 1 μM | | 7.1 | 91.6 |
| Cur 10 μM | | 7.9 | 90.6 |
| IS181 (μg/ml) + LPS + IFN-γ | 10 | 25.4 | 69.8 |
|  | 50 | 25.3 | 66.3 |
|  | 100 | 23.3 | 72.3 |
|  | 500 | 93.3 | −10.9 |
|  | 1000 | 50.6 | 39.6 |

Example 20: Signaling—Biochemical Kinase Assays

Test system: cell free assays; test items: IS181; concentrations tested: 1 ng/ml-5000 μg/ml; Kinases: a) Cell free assays: EGFR (ErbB1); FLT1 (VEGFR1); JAK1; JAK3 MAP2K1 (MEK1); PDGFRA (PDGFR alpha); PRKCA (PKC alpha); b) cell based assay: JAK-STAT. IS181 demonstrated inhibition of MAPK1 (MEK1) by 23%-49% in the concentration range of 10 μg/ml-5000 μg/ml. At 10 μg/ml, IS 181 demonstrated inhibition of EGFR (ErbB1), JAK1, JAK3 and PRKCA (PKC alpha) by 43%, 14%, 13% and 20% respectively (Table-18).

TABLE 18

| Concentration | EGFR (Erb-364B1) | FLT1 (VEGFR1) | JAK1 | JAK3 | MAP2K1 (MEK1) | PDGFRA (PDGFR alpha) | (PRKCA (PKC alpha) |
|---|---|---|---|---|---|---|---|
| 5000 μg/ml | −364 | −578 | −647 | −501 | −81 | −332 | −297 |
| 2000 μg/ml | −155 | −224 | −457 | −362 | −16 | −147 | −80 |
| 1000 μg/ml | −87 | −110 | −264 | −198 | 13 | −81 | −19 |

TABLE 18-continued

| Concentration | EGFR Erb-364B1) | FLT1 (VEGFR1) | JAK1 | JAK3 | MAP2K1 (MEK1) | PDGFRA (PDGRFR alpha) | (PRKCA (PKC alpha) |
|---|---|---|---|---|---|---|---|
| 500 µg/ml | −56 | −44 | −185 | −142 | 23 | −49 | −17 |
| 250 µg/ml | −29 | −28 | −93 | −72 | 30 | −26 | −8 |
| 100 µg/ml | −12 | −16 | −42 | −24 | 26 | −10 | 8 |
| 50 µg/ml | 43 | 44 | 14 | 13 | 49 | 8 | 20 |

Example 21: Protective Effect Against UVB Damage

Effect on Cyclobutane Pyrimidine Dimers (CPD); Effect on 8-oxo-G formation: Cell line: HaCaT (human keratinocytes); test items: IS 181; concentration range: 0.1-100 µg/ml (Duplicate wells). Method of estimation: Plating of cells; Sera starvation with 0.1% FBS (24 hours); treatment of cells with test items (24 hours); UVB damage (30 mJ/cm2)+Test items addition (24 hours); Cyclobutane pyrimidine dimers (CPD) and 8-oxo-G estimation using ELISA. Positive control: Nicotinamide. _IS 181 demonstrated 28% and 26% decrease in CPD at concentrations corresponding to 10 µg/ml and 100 µg/ml respectively. A maximum of 15.5% decrease in the levels of 8-OXO-G was attained at 5 µg/ml of IS 181 (FIG. 25 and Table-19).

TABLE 19

| Concentration (µg/ml) | % Decrease in 8-OCO-G formation with respect to UVB irradiated untreated cells IS217 |
|---|---|
| 0.1 | 4.94 |
| 1 | −0.45 |
| 5 | 15.47 |
| 10 | 6.88 |
| 100 | 2.87 |

Example 22: In Vitro Combination Studies: Anthralin and IS181; Methotrexate and IS181

Cell lines: Human Keratinocytes (HaCaT); test items: IS 181; anthralin; treatment regimen; IS 181 Multiple additions (3)—72 hours; anthralin—Single addition—72 hours; concentration range: IS 181-10 µg/ml to 5000 µg/ml; anthralin—0.01 µM-5 µM; sera condition: medium containing 1% FBS. Method of estimation: HaCaT cells were plated in medium containing 10% FBS for 24 hours; the cells were then subjected to serum starvation in 1% FBS for 24 hours; the cells were treated with Anthralin and IS 181 alone and combination of Anthralin and IS 181 so as to achieve different combinations. The cells were then incubated for 72 hours. Percentage cytotoxicity was determined using MTT assay. End point: percent inhibition of cell viability/cytotoxicity. Combination of Anthralin and IS 181 exerted good synergistic effects at doses ranging from 500 µg/ml to 5000 µg/ml of IS 181 and 0.5 µM to 5 µM of Anthralin (Table-21 and 21).

TABLE 20

| | IS 181 µg/ml | 0 | 10 | 50 | 100 | 500 | 1000 | 2000 | 5000 | IC50 value of IS 181 (µg/ml) |
|---|---|---|---|---|---|---|---|---|---|---|
| Anthralin (µM) | 0 | 0 | −10.42 | −4.81 | 8.16 | 39.38 | 62.42 | 81.37 | 94.19 | 695.50 |
| | 0.01 | 0.75 | −16.17 | 0.50 | 11.81 | 38.19 | 44.68 | 77.45 | 94.18 | 872.80 |
| | 0.05 | −2.45 | −17.10 | −9.13 | 2.16 | 32.62 | 50.19 | 78.11 | 93.80 | 908.50 |
| | 0.1 | 9.41 | −5.820 | −0.902 | 9.590 | 42.541 | 61.421 | 77.186 | 94.563 | 677.600 |
| | 0.5 | 41.31 | 30.79 | 36.97 | 45.82 | 64.15 | 82.84 | 86.72 | 94.59 | 100.50 |
| | 1 | 78.92 | 83.99 | 86.37 | 89.37 | 90.57 | 91.72 | 93.31 | 94.40 | 0.001 |
| | 5 | 87.86 | 87.80 | 90.82 | 91.90 | 92.27 | 92.99 | 93.70 | 92.48 | 3.621E−08 |
| IC 50 value of Anthralin (µM) | | 0.55800 | 0.62820 | 0.58430 | 0.52210 | 0.09728 | 0.02709 | 0.00010 | 0.00000 | |

TABLE 21

| | IS.181 µg/ml | 10 | 50 | 100 | 500 | 1000 | 2000 | 5000 |
|---|---|---|---|---|---|---|---|---|
| Anthralin (µM) | 0.01 | 3.80 | 3.62 | 3.37 | 1.65 | 1.36 | 1.26 | 1.25 |
| | 0.05 | 3.91 | 3.73 | 3.47 | 1.71 | 1.42 | 1.31 | 1.31 |
| | 0.1 | 3.20 | 3.05 | 2.82 | 1.32 | 1.07 | 0.97 | 0.97 |
| | 0.5 | 1.44 | 1.35 | 1.22 | 0.34* | 0.20* | 0.14* | 0.14* |
| | 1 | 1.13 | 1.05 | 0.94 | 0.17* | 0.05* | 0.00* | 0.00* |
| | 5 | 1.13 | 1.05 | 0.94 | 0.17* | 0.05* | 0.00* | 0.00* |

*CI < 1, Synergistic effect

Example 23: In Vitro Combination with Methotrexate

Cell lines: Human Keratinocytes (HaCaT); test items: IS181; methotrexate (MTX); treatment regimen: IS 181 Multiple additions (3)—72 hours; MTX—Single addition—72 hours; concentration range: IS 181-10 µg/ml to 5000 µg/ml; MTX-0.01 µM-5 µM; sera condition: medium containing 1% FBS; method of estimation: HaCaT cells were plated in medium containing 10% FBS for 24 hours; the cells were then subjected to serum starvation in 1% FBS for 24 hours; the cells were treated with MTX and IS181 alone and combination of MTX and IS 217 so as to achieve different combinations. The cells were then incubated for 72 hours. Percentage cytotoxicity was determined using MTT assay. End point: Percent inhibition of cell viability/cytotoxicity. When HaCaT cells were treated with MTX alone in the concentration range of 0.01 µM-5 µM, 50% inhibition of cell proliferation could not be achieved (50% inhibition >5 µM). In combination with IS181 at 10 and 50 µg/ml, this effect was persistent and 50% inhibition was still not achieved. However, at 500 µg/ml of IS181, 50% inhibition was observed between 1-5 µM of MTX. Concentrations corresponding to 50% inhibition were further lowered to 0.01 µM at 1000 ug/ml of IS181 and <0.01 µM at 2000 and 5000 ug/ml of IS181 subsequently (Table-22).

TABLE 22

| | | \multicolumn{7}{c}{15181 (µg/ml)} | | | | | | |
|---|---|---|---|---|---|---|---|
| | | Alone | 10 | 50 | 500 | 1000 | 2000 | 5000 |
| MTX (µM) | Alone | | 16.7 | 17.8 | 26.9 | 82.8 | 75.0 | 96.1 |
| | 0.01 | 12.3 | 7.2 | 14.1 | 31.4 | 50.4 | 77.1 | 95.9 |
| | 0.1 | 1.9 | −1.4 | −4.8 | 30.9 | 52.3 | 74.7 | 96.1 |
| | 0.25 | 21.3 | 6.9 | 7.9 | 34.5 | 47.0 | 75.3 | 96.1 |
| | 0.5 | 23.9 | 3.4 | 14.1 | 42.3 | 46.6 | 69.7 | 96.1 |
| | 1 | 27.7 | 16.7 | 32.3 | 48.5 | 50.5 | 74.3 | 96.0 |
| | 5 | 22.0 | 25.3 | 42.2 | 59.3 | 58.0 | 74.9 | 96.2 |
| 50% Inhibition | | >5 µM | >5 µM | >5 µM | 1-5 µM | 0.01 µM | <0.01 µM | <0.01 µM |

Example 24: Preformulation Development & Determination of MFC (Maximum Feasible Concentration) of Peptides IS181 & IS217

The solution stability of peptide IS 181 was performed in four different diluents at three different temperatures for 24 hours. Results are shown in Table-23 below and FIG. 26. Four different pre-formulations of concentration 10 mg/ml were prepared and formulation assay was performed at initial and 18 hours at room temperature. Results obtained are shown in Table 24 and 25 below.

TABLE 23

| % Stability → | 2-8° C. | Room Temperature | 37° C. |
|---|---|---|---|
| Phosphate buffer pH 5.0 | 96.53 | 102.20 | 104.05 |
| Phosphate buffer pH 7.4 | 97.99 | 102.41 | 107.22 |
| 0.9% NaCl solution | 93.64 | 101.84 | 104.94 |
| Water | 94.66 | 93.99 | 98.57 |

0.9% NaCl was selected based on its stability, suitable pH and optimum osmolarity at physiological conditions.

TABLE 24

| Preformulation | % Assay Initial | % Change from initial after 18 hrs |
|---|---|---|
| 10% v/v Tween 20 in 0.9% NaCl (for IM& SC) | 99.44 | 0.21 |
| 20% v/v Glycerol in 0.9% NaCl (for IM& SC) | 97.47 | 0.25 |
| 10% v/v Propylene glycol in 0.9% NaCl (for IM& SC) | 98.78 | −0.26 |
| 0.9% NaCl (for IV) | 98.49 | −2.24 |

All the four preformulations were found stable till 18 hrs at RT but based on intended use of formulation for IV and IM/SC administration, 20% v/v Glycerol, 10% v/v PG and 0.9% NaCl were further rested for stability at higher concentration, as these have excipients more suitable for intended use.

TABLE 25

| Test Item | Final Preformulation | MFC | MFD in Balb/c mouse* | Stability of formulation at RT |
|---|---|---|---|---|
| IS181 | 10% v/v Propylene glycol in 0.9% NaCl (for IM& SC) | >25.0 mg/ml | 50 mg/kg (i.m.) 100 mg/kg (sc) | Up to 24 hrs |
| | 0.9% NaCl (for IV) | >25.0 mg/ml | 100 mg/kg | Up to 24 hrs |

Figure 27:
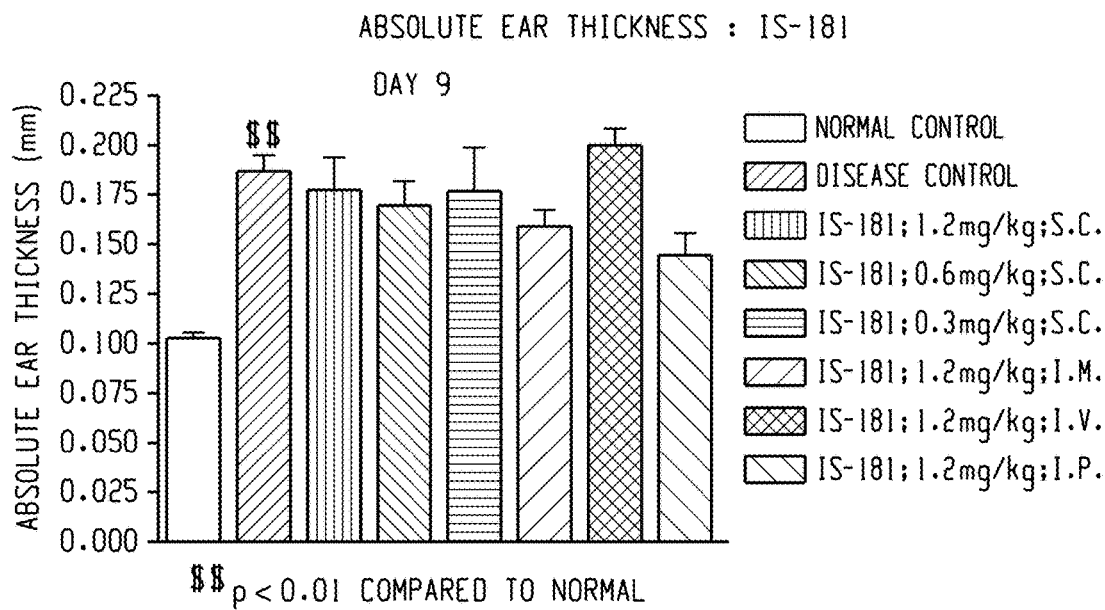
FIG. 27: Anti-psoriatic potential of DRF/TI/IS 181 in Imiquimod (IMQ) induced Psoriasis model: Data related to ear thickness.
Figure 28:
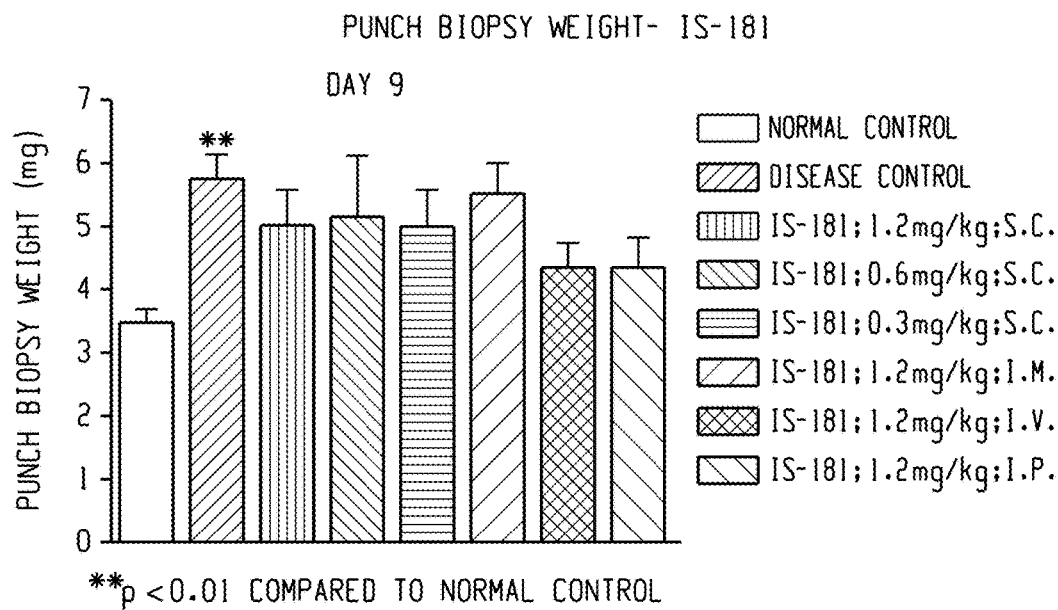
FIG. 28: Anti-psoriatic potential of DRF/TI/IS 181 in Imiquimod (IMQ) induced Psoriasis model: Data related to punch biopsy weight.
Figure 29:
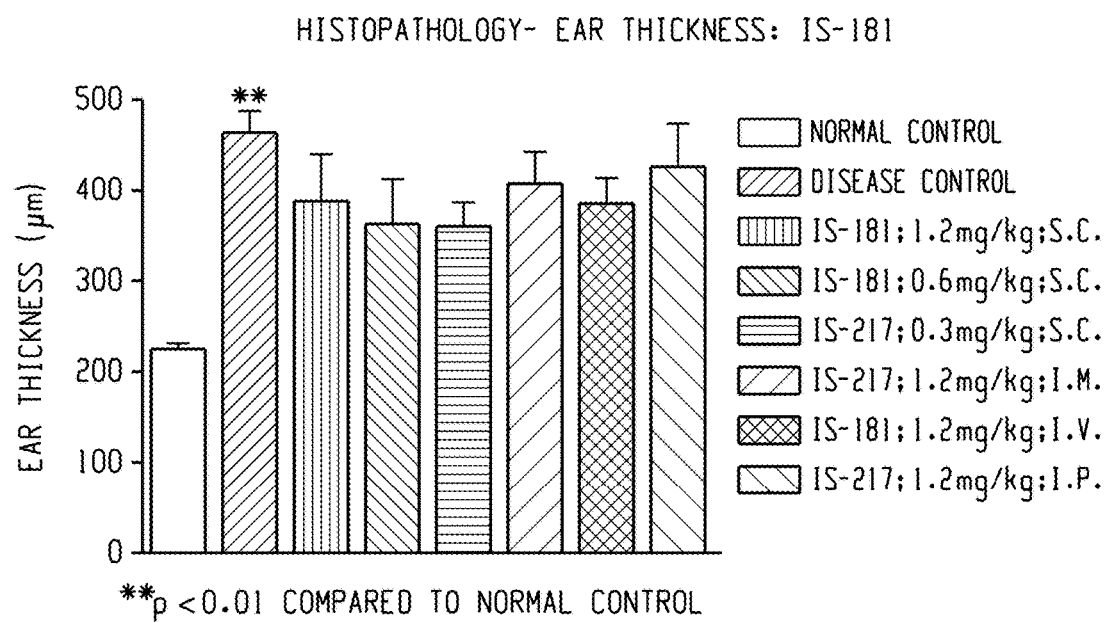
FIG. 29: Anti-psoriatic potential of DRF/TI/IS 181 in Imiquimod (IMQ) induced Psoriasis model: Data related to histopathology-ear thickness.
Figure 30:
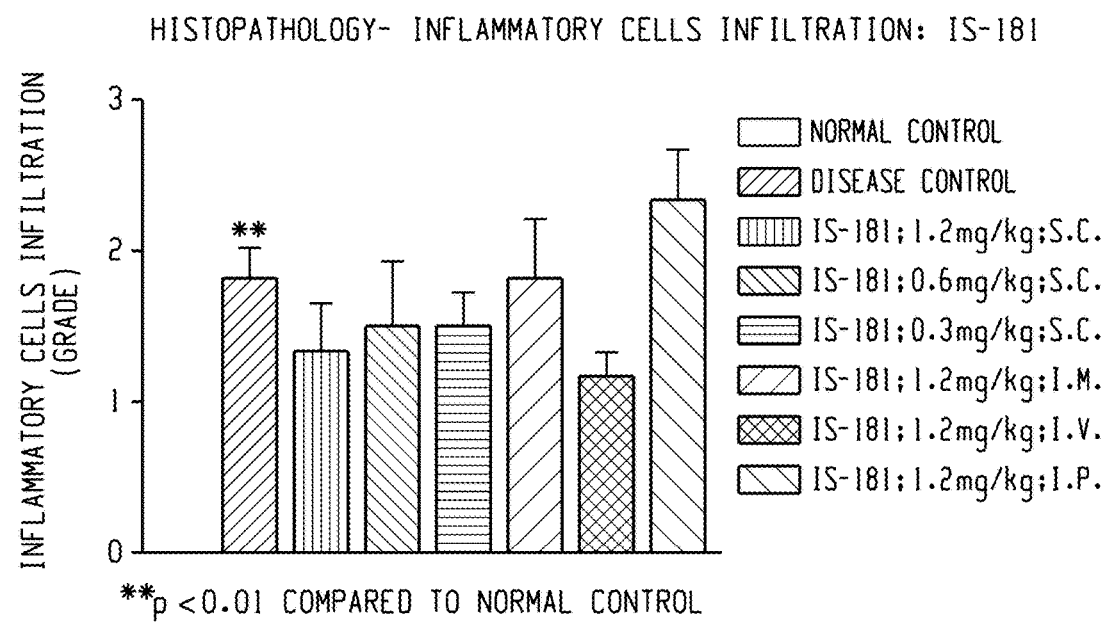
FIG. 30: Anti-psoriatic potential of DRF/TI/IS 181 in Imiquimod (IMQ) induced Psoriasis model: Data related to inflammatory cells infiltration.
Figure 31:
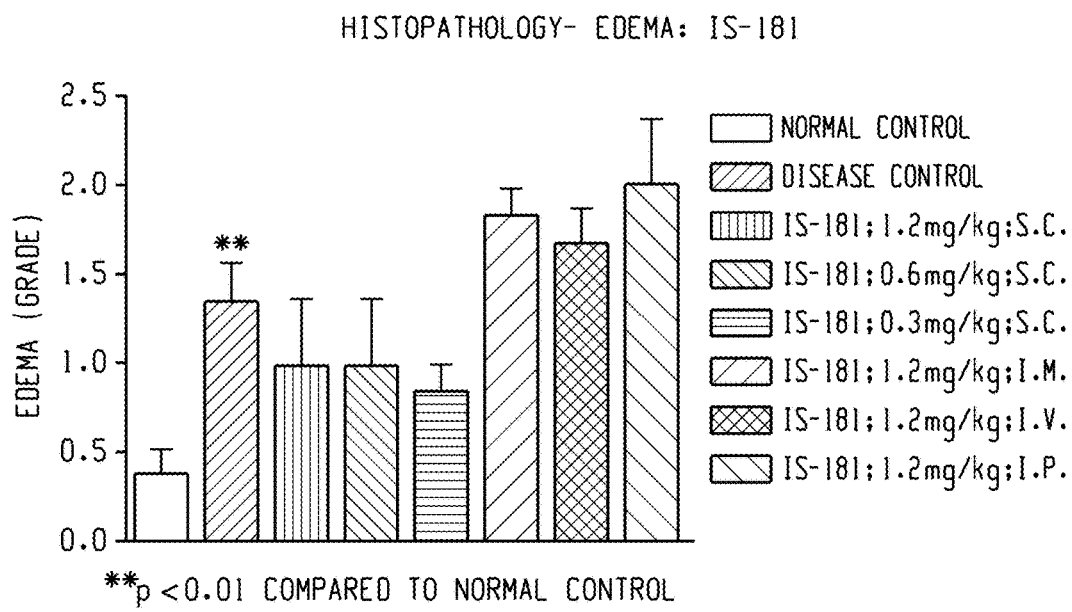
FIG. 31: Anti-psoriatic potential of DRF/TI/IS 181 in Imiquimod (IMQ) induced Psoriasis model: Data related to edema.
Figure 32:
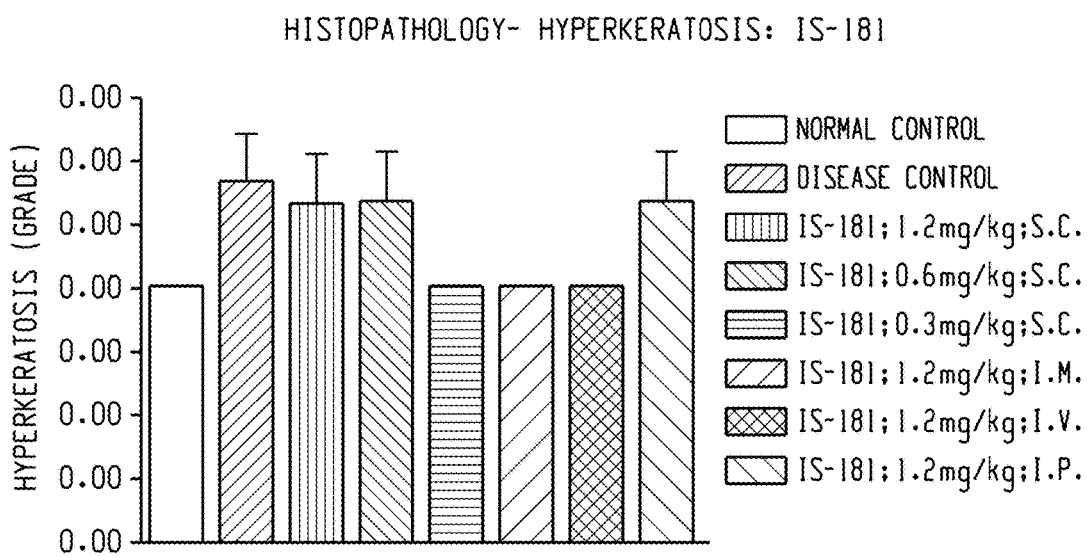
FIG. 32: Anti-psoriatic potential of DRF/TI/IS 181 in Imiquimod (IMQ) induced Psoriasis model: Data related to hyperkeratosis.
Figure 33:
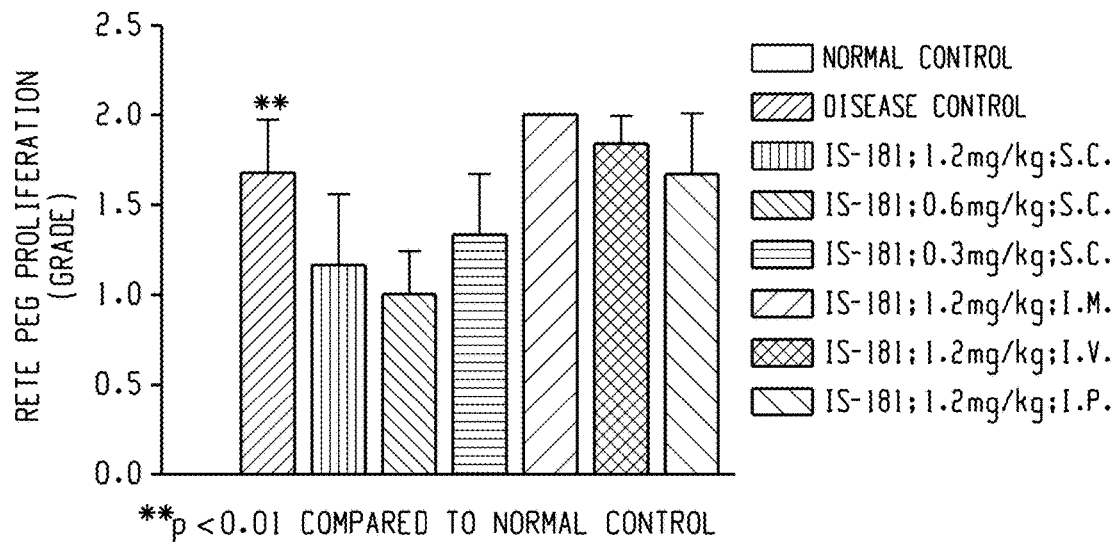
FIG. 33: Anti-psoriatic potential of DRF/TI/IS 181 in Imiquimod (IMQ) induced Psoriasis model: Data related to rete peg proliferation.
Figure 34:
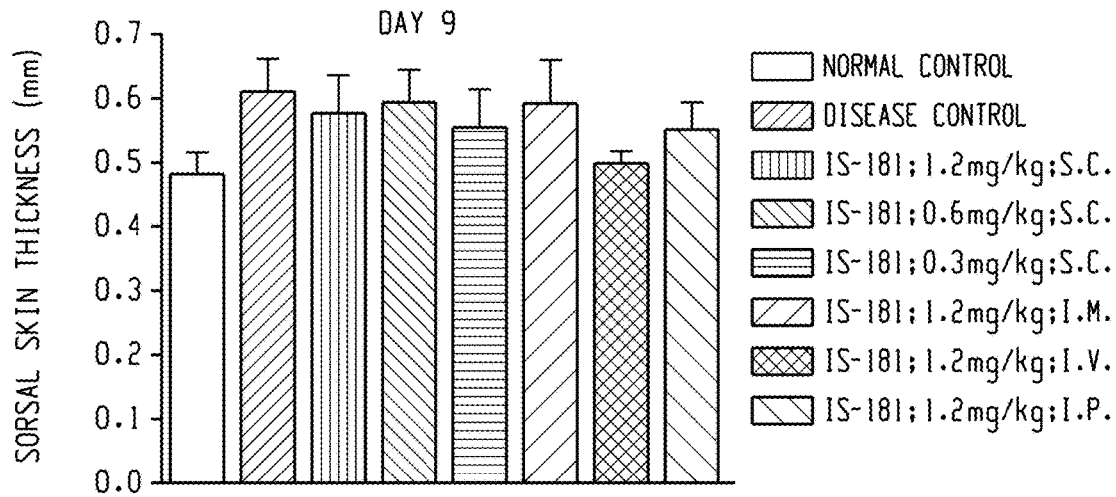
FIG. 34: Anti-psoriatic potential of DRF/TI/IS 181 in Imiquimod (IMQ) induced Psoriasis model: Data related to dorsal skin thickness.
Figure 35:
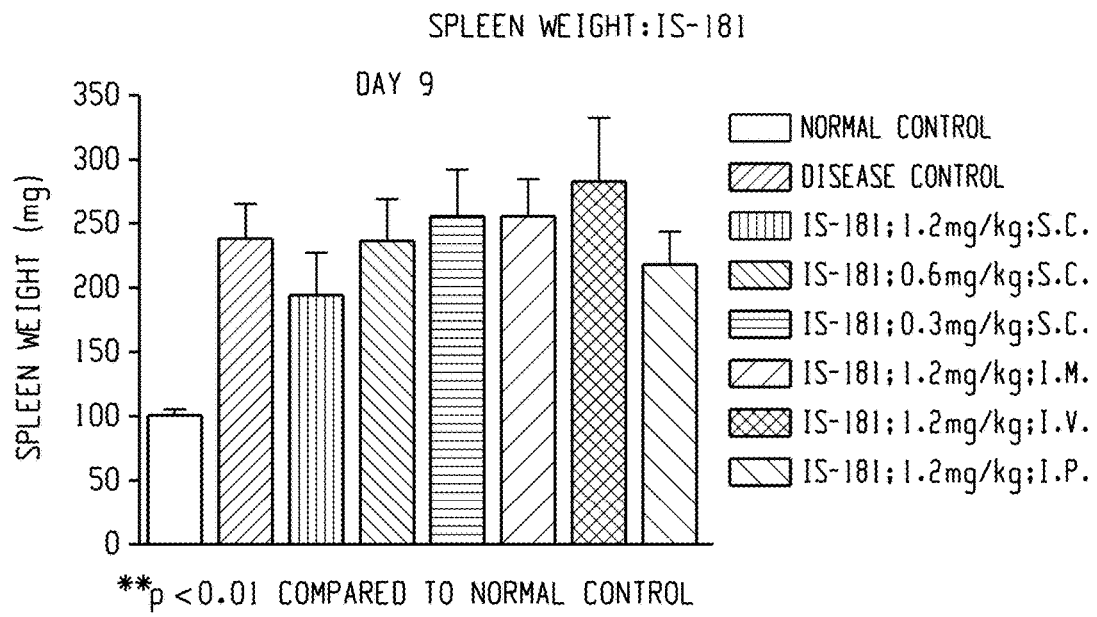
FIG. 35: Anti-psoriatic potential of DRF/TI/IS 181 in Imiquimod (IMQ) induced Psoriasis model: Data related to spleen weight.
Figure 36:
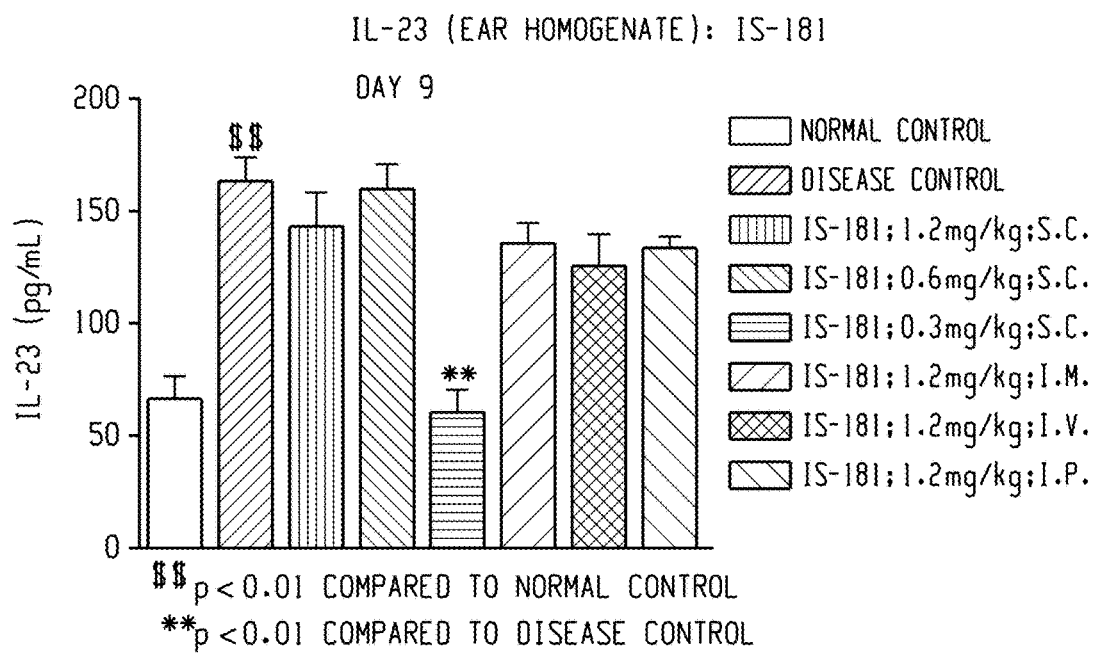
FIG. 36: Anti-psoriatic potential of DRF/TI/IS 181 in Imiquimod (IMQ) induced Psoriasis model: Data related to IL-23 (ear homogenate).
Figure 37:
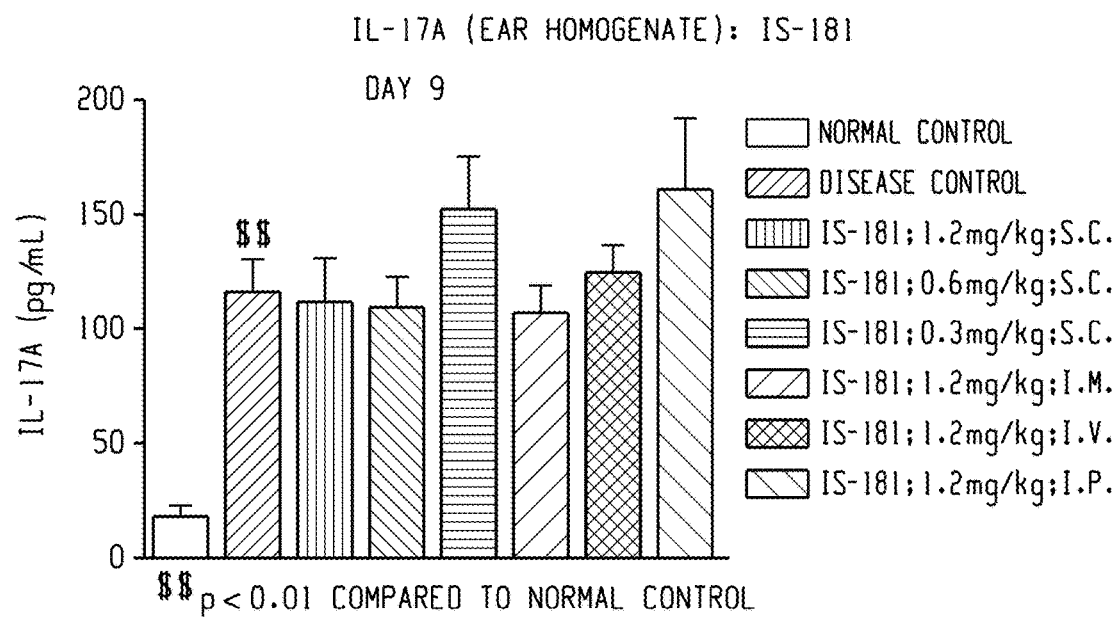
FIG. 37: Anti-psoriatic potential of DRF/TI/IS 181 in Imiquimod (IMQ) induced Psoriasis model: Data related to IL-17A (ear homogenate).
Figure 38:
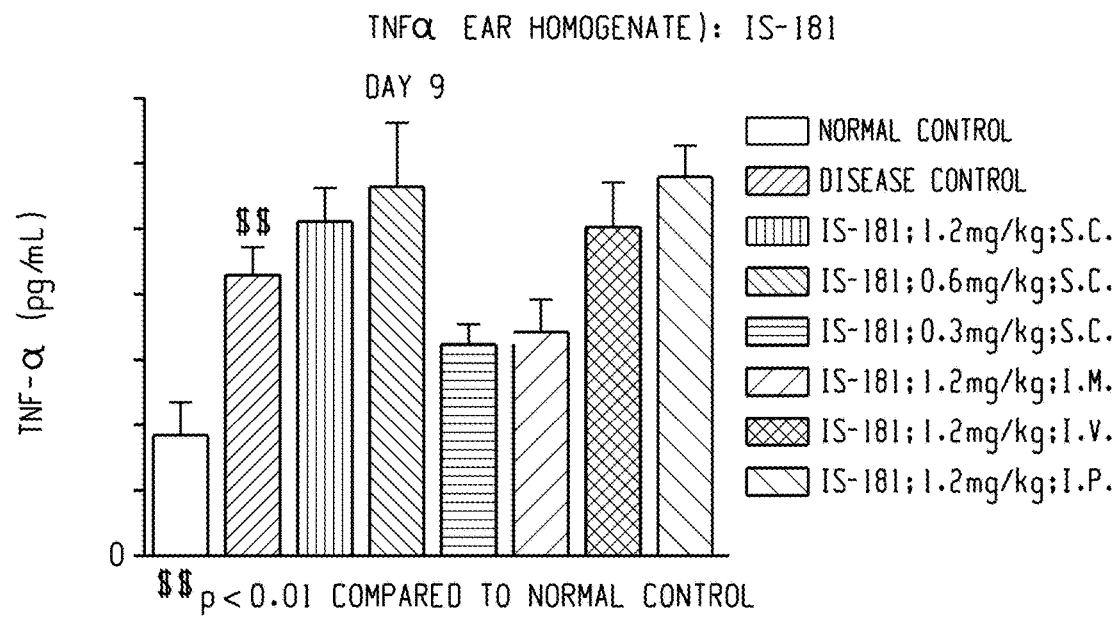
FIG. 38: Anti-psoriatic potential of DRF/TI/IS 181 in Imiquimod (IMQ) induced Psoriasis model: Data related to TNF-α (ear homogenate).
Figure 39:
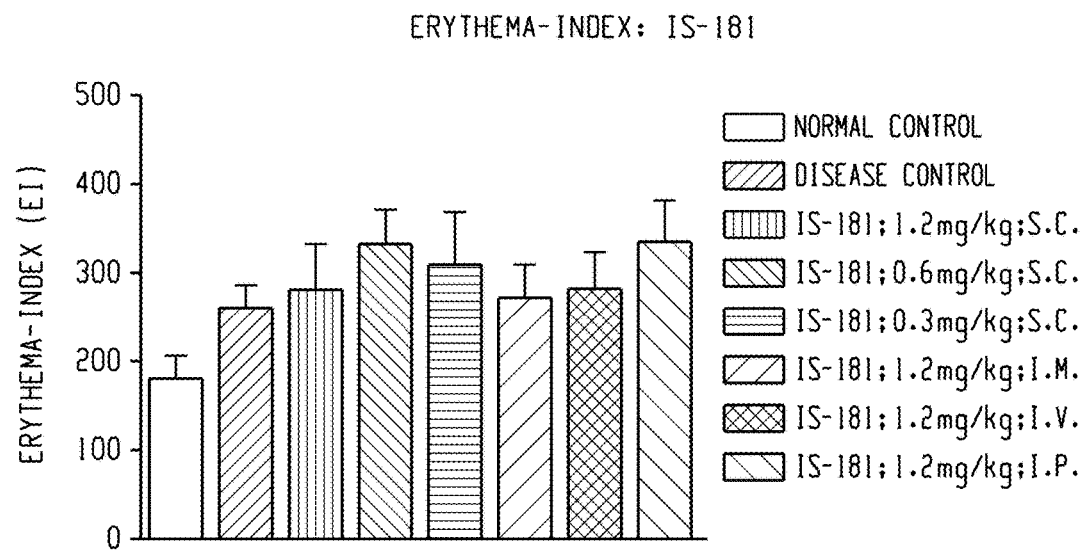
FIG. 39: Anti-psoriatic potential of DRF/TI/IS 181 in Imiquimod (IMQ) induced Psoriasis model: Data related to erythema index.
Figure 40:
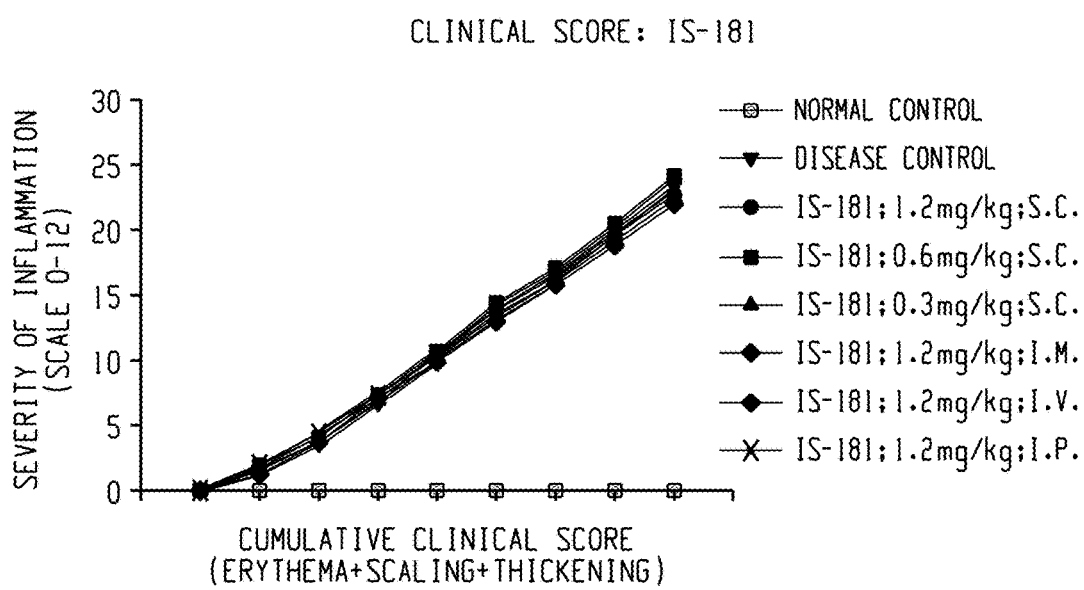
FIG. 40: Anti-psoriatic potential of DRF/TI/IS 181 in Imiquimod (IMQ) induced Psoriasis model: Data related to IL-23 (ear homogenate).
Figure 41:
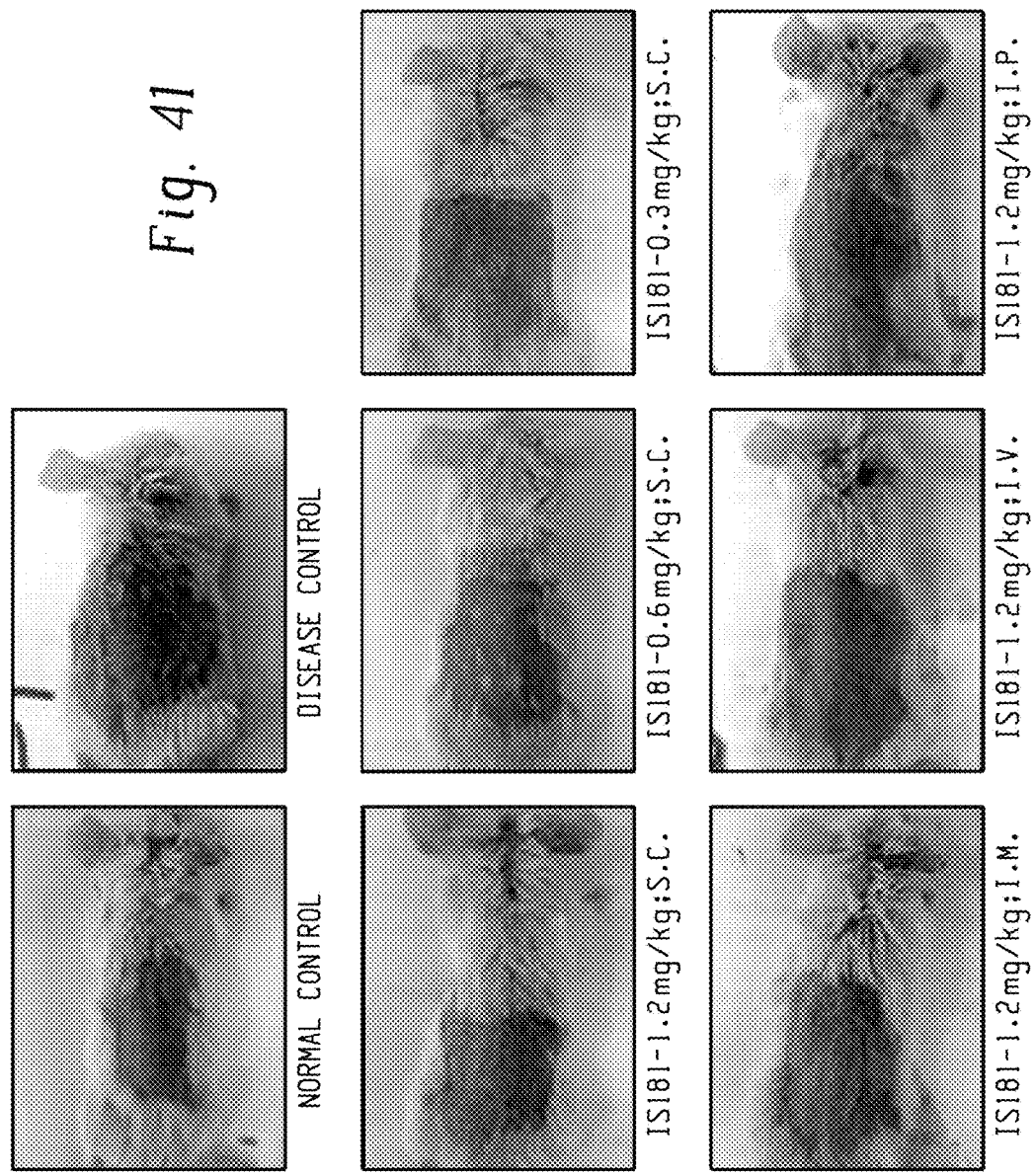
FIG. 41: Anti-psoriatic potential of DRF/TI/IS 181 in Imiquimod (IMQ) induced Psoriasis model: Gross pictures.

Example-25: Evaluation of Anti-Psoriatic Potential of DRF/TI/IS-181 in Imiquimod (IMQ) Induced Psoriasis Model Using BALB/C Mice The Experiment was carried out in Imiquimod (IMQ) induced psoriasis model in mice. The IMQ treated animals showed significant disease induction compared to normal control. The diseased animals were treated with peptides through three different routes viz s.c., i.m. and i.v. There was a trend in animals treated with IS-181 through s.c. in ear thickness (life phase), punch biopsy, spleen weight and histopathology. No trend was observed in IL-23 levels, however the animals treated with 0.3 mg/kg showed 62.35% reduction in IL-23 compared to disease control. However no trend was observed in IL-17A. In addition to that the animals treated with IS-181 at 0.3 mg/kg s.c. and 1.2 mg/kg i.m. showed 24.98% showed 21.28% reduction in TNFα respectively compared to disease control. Conclusions: The animals treated with IS-181 by s.c. showed mild reduction in ear thickness compared to disease control. And also 1.2 mg/kg i.m. and i.p treated groups also showed mild reduction in ear thickness (FIG. 27). Across the groups (except 1.2 mg/kg, i.m. treated) showed mild reduction in punch biopsy weight, however which was not significant (FIG. 28). The animals treated with IS-181 0.3 mg/kg, s.c. showed maximum reduction in ear thickness and the trend was similar as observed in ear thickness (life phase) (FIG. 29). The animals treated with IS-181 s.c. (1.2, 0.6 and 0.3 mg/kg) and 1.2 mg/kg i.v. showed reduction in inflammatory cells infiltration compared to disease control (FIG. 30). The animals treated with IS-181 s.c. (1.2, 0.6 and 0.3 mg/kg) showed reduction in edema compared to disease control (FIG. 31). Among the animals treated with IS-181 s.c., 0.3 mg/kg treated groups showed maximum effect. And 1.2 mg/kg i.m. and i.v. treated groups also showed reduction in hyperkeratosis (FIG. 32). The animals treated with IS-181 s.c. (at 1.2, 0.6 and 0.3, mg/kg) showed reduction in Rete peg proliferation (FIG. 33). Across the groups (except 0.6 mg/kg s.c. and 1.2 mg/kg i.m. treated) showed mild reduction in dorsal skin thickness, however which was not significant (FIG. 34). There was a trend in the groups treated with the peptide by s.c. route, 1.2 mg/kg treated group showed maximum reduction in spleen weight, however which was not significant. And also the animals treated with the peptide by i.p showed mild reduction in spleen weight (FIG. 35). No trend was observed in IL-23 levels, however the animals treated with 0.3 mg/kg showed 62.35% reduction in IL-23 levels compared to disease control (FIG. 36). No changes in IL-17A across the treated groups (FIG. 37). The animals treated with IS-181 at 0.3 mg/kg s.c. showed 24.98% and 1.2 mg/kg i.m. showed 21.28% reduction in TNFα compared to disease control (FIG. 38). No changes in erythema index across the treated groups (FIG. 39). No substantial changes in clinical score across the treated groups (FIG. 40). Reference is also directed to FIG. 41 which shows the Gross pictures of IS-181. Thus, there was a trend in animals treated with IS-181 through s.c. in ear thickness (life phase), punch biopsy, spleen weight and histopathology. No trend was observed in IL-23 levels, however the animals treated with 0.3 mg/kg showed 62.35% reduction in IL-23 compared to disease control. In addition to that the animals treated with IS-181 at 0.3 mg/kg s.c. and 1.2 mg/kg i.m. showed 24.98% showed 21.28% reduction in TNFα respectively compared to disease control. In the view of this, it may be worth to explore the potency of the peptide for the diseases where TNFα playing central role in pathogenesis.

Example 26: Anti-Inflammatory Activity

Cell line: RAW264.7 (Mouse macrophages); TI treatment regimen: Pretreatment for 2 h; TI Concentration range: 0.1 μg/ml-500 μg/ml (duplicate wells); LPS stimulation: 100 ng/ml; Time point for supernatants collection: 24 h; Method of estimation: ELISA; Positive control: Dexamethasone

TABLE 26

Effect on secretiion of cytokines by LPS stimulation @ 24 h post treatment

| | | TNF-α | | IL-6 | | IL-1-β | |
|---|---|---|---|---|---|---|---|
| Sample | Conc | Conc (pg/ml) | % decrease with respect to LPS | Conc (pg/ml) | % decrease with respect to LPS | Conc (pg/ml) | % decrease with respect to LPS |
| Untreated | NA | 311.4 | NA | 133.9 | NA | 6.6 | NA |
| LPS | 100 ng/ml | 2887.2 | NA | 2124.6 | NA | 22.1 | NA |
| IS181 + LPS | 0.1 μ/ml | 1190.3*** | 58.8 | 908.7*** | 57.2 | 2.2 | 90.0 |
| | 1 μ/ml | 1960.5*** | 32.1 | 1248.3*** | 41.2 | 15.4 | 30.3 |
| | 5 μ/ml | 1906.1*** | 34.0 | 1565.9*** | 26.3 | 10.2 | 53.7 |
| | 10 μ/ml | 1149.0*** | 60.2 | 501.5*** | 76.4 | 6.2 | 71.9 |
| | 100 μ/ml | 2379.2* | 17.6 | 1371.8*** | 35.4 | 12.7 | 42.4 |
| | *500 μ/ml | 1779.9*** | 38.4 | 669.1*** | 68.5 | 6.1 | 72.6 |

NA = Not applicable;
***$p < 0.001$,
**$p < 0.01$,
*$p < 0.05$ (significantly different from the LPS-treated control; group) Statistical differences between control and treatment groups were determined using GRAPHPAD PRISM 4.0, one-way ANOVA with Bonferroni's Multiple Comparison post test.

TABLE 27

Effect of positive control (Dexamethasone)

| | | TNF-α | | IL-6 | | IL-1-β | |
|---|---|---|---|---|---|---|---|
| Sample | Conc | Conc (pg/ml) | % decrease with respect to LPS | Conc (pg/ml) | % decrease with respect to LPS | Conc (pg/ml) | % decrease with respect to LPS |
| Untreated | NA | 311.4 | NA | 133.9 | NA | 6.6 | NA |
| LPS | 100 ng/ml | 2887.2 | NA | 2124.6 | NA | 22.1 | NA |
| | 0.5 μg/ml | 451.7*** | 54.1 | 567.6** | 45.9 | 9.6* | 53.6 |
| Dexamethas one + LPS | 1 μg/ml | 291.8*** | 70.4 | 405.9*** | 61.3 | 11.4* | 44.6 |
| | 10 μg/ml | 283.1*** | 71.2 | 291.2*** | 72.3 | 12.6* | 39.0 |

NA = Not applicable;
***$p < 0.001$,
**$p < 0.01$,
*$p < 0.05$ (significantly different from the LPS-treated control group) Statistical differences between control and treatment groups were determined using GRAPHPAD PRISM 4.0, one-way ANOVA with Bonferroni's Multiple Comparison post test IS181 demonstrated TNF-α inhibition as compared to LPS stimulated levels at all the concentrations tested. In the concentration range of 0.1 μg/ml-500 μg/ml, TNF-α secretion was downregulated by 17.6%-60.2%. At all the concentrations tested, there was a downregulation of IL-6 secretion by IS181. In the concentration range of 0.1 μg/ml-500 μg/ml, IS181 showed inhibition of IL-6 secretion by 26.3%-76.4% as compared to LPS treated cells. IS181 demonstrated IL-1-β inhibition as compared to LPS stimulated levels at all the concentrations tested. In the concentration range of 0.1 μg/ml-500 μg/ml, 30.3%-90% decrease in IL-1-β level was exhibited by IS181.

Example 27: Anti-Inflammatory Activity

Cell line: HaCaT (Human Keratinocytes); TI Treatment regimen: Pretreatment for 2 h; TI Concentration range: 0.1 μg/ml-100 μg/ml (duplicate wells); TNF-α stimulation: 20 ng/ml; LPS+PMA stimulation: 10 μg/ml LPS+40 ng/ml PMA; Time point for supernatants collection: 24 h; Method of estimation: ELISA; Positive control: Dexamethasone

TABLE 28

Effect on secretion of cytokines by TNF-α/(LPS + PMA) stimulation @ 24 h post treatment

| Sample | Conc | TNF-α Conc (pg/ml) | % decrease with respect to TNF-α | IFN-γ Conc (μ/ml) | % decrease with respect to TNF-α | TARC Conc (pg/ml) | % decrease with respect to TNF-α |
|---|---|---|---|---|---|---|---|
| Untreated | NA | 0 | NA | 30.0 | NA | 39.1 | NA |
| TNF-α | 20 ng/ml | 21140.8 | NA | 47.6 | NA | 60.5 | NA |
| IS181 + TNF-α | 0.1 μg/ml | 22731.8 | −7.5 | 30.7*** | 35.6 | 43.2 | 28.6 |
| | 1 μg/ml | 19924.1 | 5.8 | 30.1*** | 36.7 | 53.6 | 11.3 |
| | 5 μg/ml | 22852.1 | −8.1 | 28.6*** | 40.1 | 59.5 | 1.5 |
| | 10 μg/ml | 24469.9 | −15.7 | 34.7*** | 27.1 | 57.3 | 5.3 |
| | 100 μg/ml | 25125.0 | −18.8 | 32.4*** | 32.0 | 74.1 | −22.6 |

| Sample | Conc | IL-6 Conc (pg/ml) | % decrease with respect to LPS + PMA | IL-8 Conc (pg/ml) | % decrease with respect to LPS + PMA | TSLP Conc (pg/ml) | % decrease with respect to LPS + PMA |
|---|---|---|---|---|---|---|---|
| Untreated | NA | 8.1 | NA | 214.7 | NA | 75.3 | NA |
| LPS + PMA | 10 μg/ml + 40 ng/ml | 15.0 | NA | 392.0 | NA | 124.2 | NA |
| IS181 + LPS + PMA | 0.1 μg/ml | 23.7 | −58.3 | 357.4 | 8.8 | 62.9*** | 49.4 |
| | 1 μg/ml | 26.7 | −78.5 | 314.5 | 19.8 | 64.7*** | 47.9 |
| | 5 μg/ml | 23.4 | −56.5 | 375.3 | 4.3 | 66.6*** | 46.4 |
| | 10 μg/ml | 22.1 | −48.0 | 316.1 | 19.4 | 57.6*** | 53.6 |
| | 100 μg/ml | 39.0 | −160.6 | 463.1 | −18.1 | 62.4*** | 49.8 |

NA = Not applicable; Negative values represent no inhibition of cytokine;
***$p < 0.001$,
**$p < 0.01$,
*$p < 0.05$ (significantly different from the LPS-treated control group) Statistical differences between control and treatment groups were determined using GRAPHPAD PRISM 4.0, one-way ANOVA with Bonferroni's Multiple Comparison post test.

TABLE 29

Effect of positive control (Dexamethasone)

| Sample | Conc | TNF-α Conc (pg/ml) | % decrease with respect to TNF-α | IFN-γ Conc (pg/ml) | % decrease with respect to TNF-α | TARC Conc (pg/ml) | % decrease with respect to TNF-α |
|---|---|---|---|---|---|---|---|
| Untreated | NA | 0 | NA | 30.0 | NA | 39.1 | NA |
| TNF-α | 20 ng/ml | 21140.8 | NA | 47.6 | NA | 60.5 | NA |
| Dexamethasone + TNF-α | 1 μM | 17423.9 | 17.6 | 31.2*** | 34.5 | 52.5 | 13.2 |
| | 10 μM | 14536.0 | 31.2 | 35.5** | 25.4 | 52.3 | 13.5 |
| | 25 μM | 20138.0 | 4.7 | 32.8** | 31.2 | 52.3 | 13.5 |

| Sample | Conc | IL-6 Conc (pg/ml) | % decrease with respect to LPS + PMA | IL-8 Conc (pg/ml) | % decrease with respect to LPS + PMA | TSLP Conc (pg/ml) | % decrease with respect to LPS + PMA |
|---|---|---|---|---|---|---|---|
| Untreated | NA | 8.1 | NA | 214.7 | NA | 75.3 | NA |
| LPS + PMA | 10 μg/ml + 40 ng/ml | 15.0 | NA | 392.0 | NA | 124.2 | NA |

TABLE 29-continued

| Effect of positive control (Dexamethasone) | | | | | | | |
|---|---|---|---|---|---|---|---|
| Dexametha sone + LPS + PMA | 1 μM | 0.0*** | 100.0 | 136.9*** | 65.1 | 66.6** | 46.4 |
| | 10 μM | 0.8*** | 94.8 | 107.4*** | 72.6 | 72.1** | 41.9 |
| | 25 μM | 2.4*** | 84.2 | 125.7*** | 67.9 | 68.7** | 44.7 |

NA = Not applicable; Negative values represent no inhibition of cytokine;
***$p < 0.001$,
**$p < 0.01$,
*$p < 0.05$ (significantly different from the LPS-treated control group) Statistical differences between control and treatment groups were determined using GRAPHPAD PRISM 4.0, one-way ANOVA with Bonferroni's Multiple Comparison post test.

TNF-α:

TNF-α has been shown to play a crucial role in the pathogenesis of many chronic inflammatory disease such as: inflammatory bowel disease; rheumatoid arthritis, juvenile rheumatoid arthritis; psoriatic arthritis; osteoarthritis; refractory rheumatoid arthritis, chronic non-rheumatoid arthritis; osteoporosis/bone resorption; coronary heart disease; vasculitis; ulcerative colitis; psoriasis; adult respiratory distress syndrome; diabetes; skin delayed type hypersensitivity disorders; Alzheimer's disease.

IL-17/IL-23:

Interleukin-17 in the pathogenesis of several immune-inflammatory diseases including: psoriasis; psoriatic arthritis; rheumatoid arthritis. Targeting of IL-23 or the IL-23 receptor or IL-23 axis is a potential therapeutic approach for autoimmune diseases including: psoriasis; inflammatory bowel disease; rheumatoid arthritis; multiple sclerosis.

Methotrexate:

Methotrexate is approved for treatment of psoriasis and rheumatoid arthritis. It is also approved for multiple cancers such as Acute lymphoblastic leukemia; Breast cancer; Gestational trophoblastic disease; Head and neck cancer (certain types); Lung cancer; Mycosis fungoides (a type of cutaneous T-cell lymphoma) that is advanced; Non-Hodgkin lymphoma that is advanced; Osteosarcoma that has not spread to other parts of the body (It is used following surgery to remove the primary tumor). Off label-an ectopic pregnancy (often known as a "tubal" pregnancy); Crohn's disease; psoriatic arthritis (see Methotrexate and Psoriatic Arthritis for more information); dermatomyositis (a connective tissue disease that involves muscles and skin). Methotrexate is also used to treat, systemic lupus, and severe asthma.

In view of the examples provided herein (TNF alpha, IL 6, IL 17A, IL 23 inhibition & synergy with Methotrexate), IS 181 can be used in following areas: rheumatoid arthritis; inflammatory bowel disease; osteoarthritis; osteoporosis/bone resorption; ulcerative colitis; respiratory distress syndrome; diabetes; skin delayed type hypersensitivity disorders; Alzheimer's disease.

In view of the data provided herein (UV protection), IS 171 can be used in the areas including Actinic Keratosis, Malignant melanoma and Cosmetic products for UV protection. In view of the data provided herein (Anti-angiogenesis), IS 1 can be used in the areas including in tumors; rheumatoid arthritis, Ischemic retinopathies, Age-dependant macular degeneration, chronic transplant rejection; psoriasis, psoriatic Arthritis, atherosclerosis, restenosis, obesity, pulmonary hypertension, chronic respiratory diseases, cerebral ischemia, dementia, atopic dermatitis, Actinic keratosis and vascular malformations.

In view of the data provided herein (pro-apoptotic and anti-proliferative), IS 181 can be used in the areas including multiple myeloma, malignant melanoma, non-melanoma skin cancers, other oncology indications and autoimmune disease including psoriasis where dysfunctional apoptosis is reported.

I claim:

1. A method for the treatment of atopic dermatitis, psoriasis, and melanoma, the method comprising administering a therapeutically effective amount of a peptide consisting of amino acid sequence of SEQ ID NO: 1 to a patient in need of such treatment.

2. The method of claim 1 wherein the peptide is administered in monotherapy, in combination therapy, conjugate therapy and/or in a delivery system selected from a pegylation system, a liposome system, or a nanoemulsion system.

3. The method as claimed in claim 1 wherein said administration is selected from oral, subcutaneous, topical, intraperitoneal, intravenous, or combination thereof.

* * * * *